(12) United States Patent
Hansen

(10) Patent No.: US 8,481,553 B2
(45) Date of Patent: Jul. 9, 2013

(54) ANTIMETASTATIC COMPOUNDS

(75) Inventor: Marc Hansen, Pleasant Grove, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 13/639,397

(22) PCT Filed: Apr. 6, 2011

(86) PCT No.: PCT/US2011/031448
§ 371 (c)(1),
(2), (4) Date: Oct. 4, 2012

(87) PCT Pub. No.: WO2011/127192
PCT Pub. Date: Oct. 13, 2011

(65) Prior Publication Data
US 2013/0035348 A1  Feb. 7, 2013

Related U.S. Application Data

(60) Provisional application No. 61/321,324, filed on Apr. 6, 2010, provisional application No. 61/322,383, filed on Apr. 9, 2010, provisional application No. 61/325,682, filed on Apr. 19, 2010.

(51) Int. Cl.
*A01N 43/90* (2006.01)
*A61K 31/519* (2006.01)

(52) U.S. Cl.
USPC ...................................................... 514/262.1

(58) Field of Classification Search
None
See application file for complete search history.

(56) References Cited

U.S. PATENT DOCUMENTS

| | | | |
|---|---|---|---|
| 5,968,952 A | 10/1999 | Venet et al. | |
| 2006/0009493 A1 | 1/2006 | Koenig et al. | |
| 2006/0035907 A1 | 2/2006 | Christensen et al. | |
| 2009/0163545 A1* | 6/2009 | Goldfarb | 514/312 |
| 2010/0184754 A1 | 7/2010 | Renhowe et al. | |

FOREIGN PATENT DOCUMENTS

WO  WO 2012/027392  3/2012

OTHER PUBLICATIONS

Zhen-Hua Mei et al., "Synthesis and Liquid-Crystalline Properties of Novel Compounds with 3-Fluoro-Cyanophenoxy Group," Asian Journal of Chemistry, vol. 21, No. 9 (2009), 6719-6727.*
Mohammadi et al., Crystal structure of an angiogenesis inhibitor bound to the FGF receptor tyrosine kinase domain, The EMBO Journal 17(20) pp. 5896-5904, 1998, Abstract.

* cited by examiner

*Primary Examiner* — Craig Ricci
*Assistant Examiner* — Jared D Barsky
(74) *Attorney, Agent, or Firm* — Brinks Hofer Gilson & Lione; Ryan L. Marshall

(57) ABSTRACT

Screening methods for identifying compounds and compounds and pharmaceutical compositions for treating and preventing cancer are disclosed. The compounds affect signal transduction downstream of the MET receptor.

16 Claims, No Drawings

ANTIMETASTATIC COMPOUNDS

REFERENCE TO EARLIER FILED APPLICATIONS

This application is a 371 national phase of PCT/US2011/031448, filed Apr. 6, 2011, and claims priority to U.S. Provisional Application No. 61/321,324, filed Apr. 6, 2010; U.S. Provisional Application No. 61/322,383, filed Apr. 9, 2010; and U.S. Provisional Application No. 61/325,682, filed Apr. 19, 2010, the disclosures of which are incorporated, in their entirety, by this reference.

TECHNICAL FIELD

The present invention relates to screening methods for agents targeting MET receptor signaling and agents and compositions identified using those screening methods as well as their anti-cancer use.

BACKGROUND

Cancer metastasis occurs when individual cancer cells in existing tumors detach from their neighbors, invade local tissues, migrate to distant sites, and establish new tumors at those locations. Epithelial tumors of epithelial origin, which account for 80% of all new cancer diagnoses, are likely to undergo metastasis. Metastasis greatly complicates treatment and increases lethality, particularly since many epithelial primary tumors are not directly life threatening. Significant interest has developed in designing strategies that reduce or prevent metastatic cellular behavior, increasing the effectiveness of existing therapies.

Initiation of metastasis is associated with mutation or expression changes of the MET receptor. MET is activated by its endogenous ligand, scatter factor, or hepatocyte growth factor (HGF). MET is a receptor tyrosine kinase. It has been demonstrated that small molecule inhibitors of MET's kinase activity can prevent the cellular response to MET activation, whether by ligand or by alterations in MET sequence or expression levels. MET inhibitors have been advanced as potential anti-cancer agents. MET signaling is also associated with resistance of cancer cells to radiation treatment. Thus, MET inhibitors can be used to increase cancer susceptibility to radiation therapies that are designed to eliminate tumors.

Signal transduction downstream of MET has not been well defined. The series of events that leads from MET receptor activation to the cellular response remains unclear. Thus, efforts to design inhibitors of MET pathway signaling at points downstream of the MET receptor have been unproductive. Such inhibitors are likely to be more broadly effective than MET inhibitors in treating cancer, as signaling from other receptor systems could converge on the same biological circuits used downstream of MET. Direct MET receptor inhibitors are limited to instances where MET signal transduction is improperly activated at the level of MET itself, while inhibitors that act on MET signaling at points downstream of MET itself will be useful where MET signaling is improperly activated at any level at or above the point of inhibition.

SUMMARY

In one aspect, methods of inhibiting cellular responses to MET receptor signaling are disclosed which includes administering a compound of formula I:

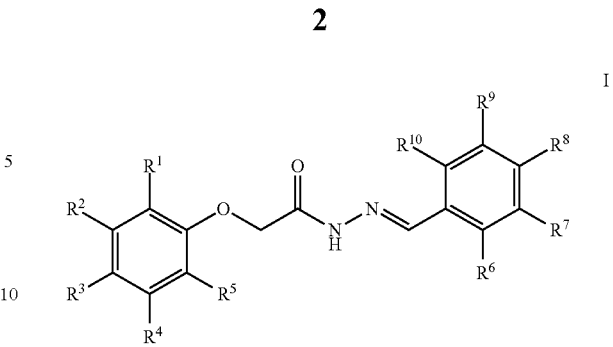

wherein each of $R^1$, $R^2$, $R^3$, $R^4$, and $R^5$ is selected from the group consisting of: H, alkyl, alkenyl, alkynyl, alkoxy, carboxy, hydroxy, halo, cyano, nitro, or together with another R group form a fused ring, and wherein each of $R^6$, $R^7$, $R^8$, $R^9$, and $R^{10}$ is selected from the group consisting of: H, alkyl, alkenyl, alkynyl, alkoxy, carboxy, carboxyalkyl, hydroxy, halo, cyano, or together with another R group form a fused ring, and pharmaceutically acceptable salts thereof.

In another aspect, methods of inhibiting cellular responses to MET receptor signaling are disclosed which includes administering a compound of formula II:

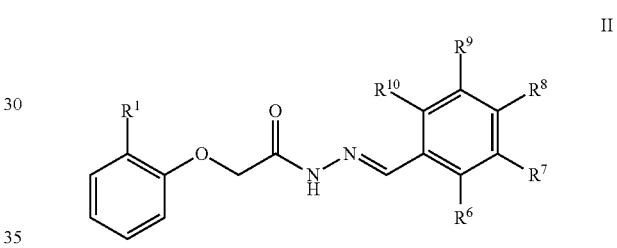

wherein $R^1$ is selected from alkyl, alkenyl, alkoxy, and cyano, and wherein each of $R^6$, $R^7$, $R^8$, $R^9$, and $R^{10}$ is selected from the group consisting of: H, alkyl, alkenyl, alkynyl, alkoxy, carboxy, carboxyalkyl, hydroxy, halo, cyano, nitro, or together with another R group form a fused ring, and pharmaceutically acceptable salts thereof.

In another aspect, methods of inhibiting cellular responses to MET receptor signaling are disclosed which includes administering a compound of formula A-I:

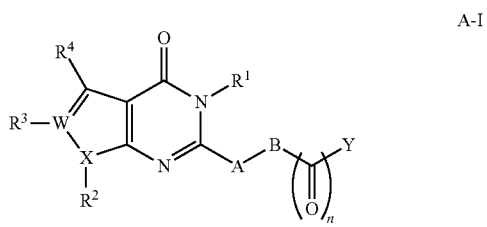

wherein $R^1$ is selected from H, phenyl, and benzyl; $R^2$ is absent or H; $R^3$ is H, absent, or together with $R^4$ forms a carbocyclic ring; $R^4$ is H, absent or together with $R^3$ forms a carbocyclic ring; X is N, S, or together with W completes a phenyl ring; W is C, N, or together with X completes a phenyl ring; A is absent or selected from S and NH; B is absent or selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

In another aspect, methods of inhibiting cellular responses to MET receptor signaling are disclosed which includes administering a compound of formula A-II:

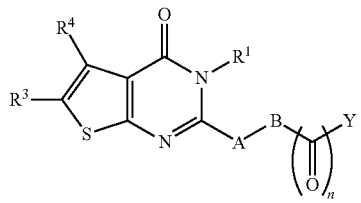

A-II wherein R¹ is selected from H, phenyl, and benzyl; R³ is H or together with R⁴ forms a carbocyclic ring; R⁴ is H or together with R³ forms a carbocyclic ring; A is absent or selected from S and NH; B is absent or selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

In another aspect, methods of inhibiting cellular responses to MET receptor signaling are disclosed which includes administering a compound of formula A-IIa or A-IIb:

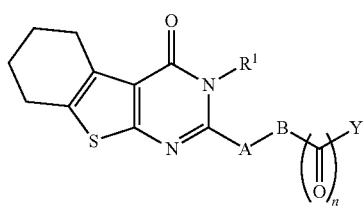

A-IIa

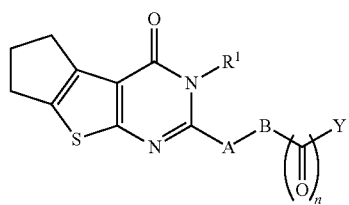

A-IIb wherein R¹ is selected from H, phenyl, and benzyl; A is absent or selected from S and NH; B is absent or selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

In another aspect, methods of inhibiting cellular responses to MET receptor signaling are disclosed which includes administering a compound of formula A-III:

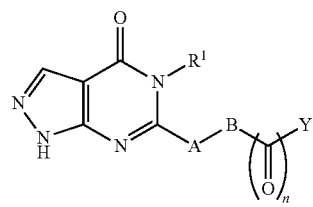

A-III wherein R¹ is selected from H, phenyl, and benzyl; A is absent selected from S and NH; B is absent or selected from alkyl and alkenyl; n is 0 or 1; Y is selected from alkyl, alkenyl, alkoxy, hydroxy, unsubstituted aryl, unsubstituted heteroaryl, substituted aryl, and substituted heteroaryl; and pharmaceutically acceptable salts thereof.

In another aspect, methods of inhibiting cellular responses to MET receptor signaling are disclosed which includes administering a compound of formula A-IV:

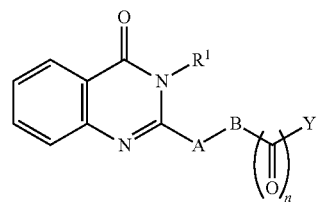

A-IV wherein R¹ is selected from H, phenyl, and benzyl; A is absent selected from S and NH; B is absent or selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

In another aspect, methods of inhibiting cellular responses to MET receptor signaling are disclosed which includes administering a compound of formula B-I:

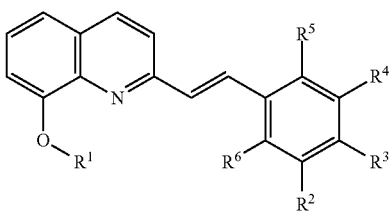

B-I wherein R¹ is selected from H, alkyl, (C=O)alkyl, and optionally substituted benzyl; R² is selected form H, alkyl, halogen, hydroxyl, alkoxy, ester, nitro, and benzyl ether or with R³ forms a heterocyclic ring; R³ is selected form H, alkyl, halogen, hydroxyl, alkoxy, ester, nitro, and benzyl ether or with one of R² and R⁴ forms a heterocyclic ring; R⁴ is selected form H, alkyl, halogen, hydroxyl, alkoxy, ester, and nitro, benzyl ether or with R³ forms a heterocyclic ring; R⁵ is selected form H, alkyl, halogen, hydroxyl, alkoxy, ester, nitro, and benzyl ether; R⁶ is selected form H, alkyl, halogen, hydroxyl, alkoxy, ester, nitro, and benzyl ether; and pharmaceutically acceptable salts thereof.

In another aspect, methods of inhibiting cellular responses to MET receptor signaling are disclosed which includes administering a compound of formula B-IIa:

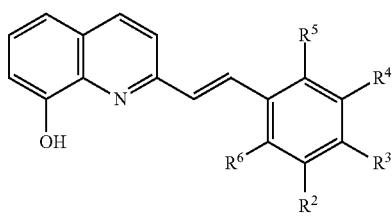

B-IIa wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, and nitro, benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; and pharmaceutically acceptable salts thereof.

In another aspect, methods of inhibiting cellular responses to MET receptor signaling are disclosed which includes administering a compound of formula B-IIb:

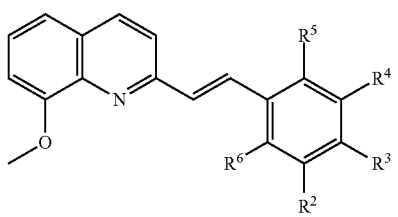

B-IIb wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; and pharmaceutically acceptable salts thereof.

In another aspect, methods of inhibiting cellular responses to MET receptor signaling are disclosed which includes administering a compound of formula B-IIc:

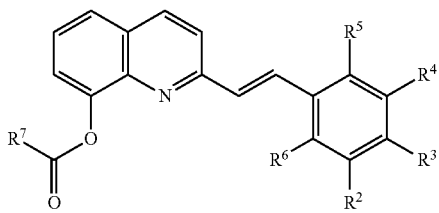

B-IIc wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; $R^7$ is alkyl; and pharmaceutically acceptable salts thereof.

In another aspect, methods of inhibiting cellular responses to MET receptor signaling are disclosed which includes administering a compound of formula B-IId:

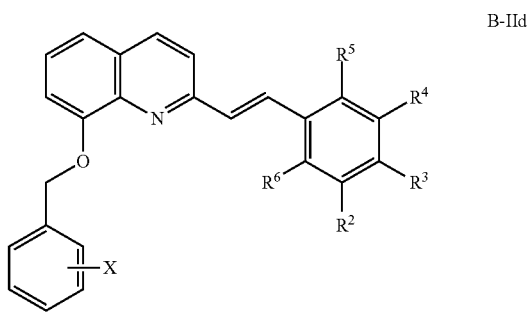

B-IId wherein X is halogen or absent; $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; and pharmaceutically acceptable salts thereof.

In another aspect, pharmaceutical compositions disclosed include those with any one or more of the compounds of formula I, II, A-I, A-II, A-IIa, A-IIb, A-III, A-IV, B-I, B-IIa, B-IIb, B-IIc, and B-IId and a pharmaceutically acceptable carrier.

In another aspect, methods of inhibiting cellular responses to MET receptor signaling are disclosed which include administering any one or more of the compounds or pharmaceutical compositions containing those compounds of formula I, II, A-I, A-II, A-IIa, A-IIb, A-III, A-IV, B-I, B-IIa, B-IIb, B-IIc, and B-IId.

In another aspect, methods of preventing or treating cancer comprising are disclosed which include administering any one or more of the compounds or pharmaceutical composition containing those compounds of formula I, II, A-I, A-II, A-IIa, A-IIb, A-III, A-IV, B-I, B-IIa, B-IIb, B-IIc, and B-IId.

In another aspect, the compounds of formula I, II, A-I, A-II, A-IIa, A-IIb, A-III, A-IV, B-I, B-IIa, B-IIb, B-IIc, and B-IId and pharmaceutical compositions with the those compounds may be used as anticancer agents, particularly by inhibiting cells' response to MET activation or by preventing cell behavior associated with epithelial-mesenchyme transition or cancer progression. Thus, the compounds and pharmaceutical formulations may be used in cancer treatment or as agents that prevent or reduce cancer progression.

In another aspect, an assay for identifying compounds that inhibit cellular responses of eukaryotic cells to c-met activation is disclosed. The method includes the steps of (a) providing a MDCK cell expressing an MET protein; (b) contacting the cell with a test compound; (c) contacting the cell with hepatocyte growth factor; (d) determining activation of the c-met pathway in the cell by measuring epithelial-mesenchymal transition of MDCK cells, wherein no appearance of detached, migratory MDCK cells is indicative of a compound that inhibits epithelial-mesenchymal transition by c-met activation, and wherein the appearance of detached, migratory MDCK cells is indicative of a compound that does not inhibit c-met induced epithelial-mesenchymal transition.

DETAILED DESCRIPTION

While the terminology used in this application is standard within the art, the following definitions of certain terms are provided to assure clarity.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "alkyl" refers to a saturated, branched or straight-chained or cyclic hydrocarbon radical (group) having at least one carbon atom including, but not limited to, saturated $C_1$-$C_6$ such as: methyl, ethyl, 1-propyl and 2-propyl, 1-butyl, 2-butyl, 2-methyl-1-propyl, 1,1-dimethylethyl, 1-pentyl, 2-pentyl, 3-pentyl, 2-methyl-1-butyl, 3-methyl-1-butyl, 2,2-dimethylpropyl, 1-hexyl, 2-hexyl, 3-hexyl, 2-methyl-1-pentyl, 3-methyl-1-pentyl, 4-methyl-1-pentyl, 3,3-dimethyl-1-butyl, 3,3-dimethyl-2-butyl, 2-ethyl-1-butyl and the like. Alkyl groups may be unsubstituted or substituted.

The term "unsaturated alkyl" refers to an alkyl radical (group) having two or more carbons with at least one unit of unsaturation. Unsaturated alkyl groups are also known as alkenyl radicals and alkynyl radicals. Alkenyl groups are analogous to alkyl groups which are saturated, but have at least one double bond (two adjacent $sp^2$ carbon atoms). Depending on the placement of a double bond and substituents, if any, the geometry of the double bond may be trans (E), or cis (Z). Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Unsaturated alkyl groups may be unsubstituted or substituted.

Examples of alkenyl radicals include, but are not limited to, vinyl, allyl, 2-methyl-2-propenyl, cis-2-butenyl, trans-2-butenyl, and acetyl, propene, 1-butene, 2-butene, 2-methylpropene, 1-pentene, 2-petnene, 2-methyl-1-butene, 2-methyl-2-butene, 3-methyl-1-butene, 1-hexene, 2-hexene, 3-hexene, 2,3-dimethyl-1-butene, 2,3-dimethyl-2-butene, 3,3-dimethyl-1-butene, 2-dimethyl-2-butene, 2-ethyl-1-butene, and the like.

Examples of dialkenyl radicals include, but are not limited to, propandiene (allene), 1,3-butadiene, 1,3-pentadiene, 1,4-pentadiene, 2-methyl-1,3-butadiene (isoprene), 3-methyl-1,2-butadiene, 1,3-hexadiene, 1,4-hexadiene, 1,5-hexadiene, 2,4-hexadiene, 2,3-dimethyl-1,3-butadiene, 2-methyl-1,3-pentadiene, 2-methyl-1,4-pentadiene, 3-methyl-1,4-pentadiene, 4-methyl-1,3-pentadiene, 3-methyl-1,3-pentadiene, and the like.

Examples of alkynyl radicals include, but are not limited to, 1-butyne, 2-butyne, 1-pentyne, 2-pentyne, 4-methyl-pent-1-yne, 1-hexyne, 2-hexyne, 3-hexyne, 3,3-dimethyl-1-butyne, 1-heptyne, 2-heptyne, 3-heptyne, 5-methyl-1-hexyne, 1-octyne, 2-octyne, 3-octyne, 4-octyne, 1-nonyne, 1-decyne, 5-decyne and 1-dodecyne, 1-pentadecyne and the like. Alkenyl and alkynyl groups may be unsubstituted or substituted.

As used herein, "unsaturated alkyl" may also include mixed alkenyl and alkynl groups. An unsaturated hydrocarbon may thus include subunits of double bonds and subunits of triple bonds. Examples of these mixed alkenyl and alkynl groups include 2-methyl-1-buten-3-yne, 2-methyl-1-hexen-3-yne and the like. Mixed alkenyl and alkynl groups may be unsubstituted or substituted.

As used herein, "alkoxy" refers to an OR group, where R is alkyl or substituted alkyl. The term "lower alkoxy" refers alkoxy groups having two to ten carbon atoms.

As used herein, "cycloalkyl" as a group or as part of another group refers to saturated or partially saturated mono-, bi-, or polycyclic carbocycle of 3-16 or 5-12 carbon atoms, such as a saturated monocyclic ring. Examples of which include cyclopentyl, cyclohexyl, cycloheptyl or cyclooctyl, for instance cyclohexyl, or saturated bicyclic ring, such as a "monocycle" as defined above which is fused with a saturated ring moiety of 5 to 8 ring atoms, e.g. with cyclohexyl moiety. Alternatively, partially saturated "cycloalkyl" is as defined above for saturated cycloalkyl except that it contains one to two double or triple bond(s) in the ring structure thereof, whereby in case of a bicycle also systems wherein a saturated monocycle is fused with an aromatic ring moiety, e.g. benzo moiety, are covered.

As used herein, "aryl" refers to an aromatic group which has at least one ring having a conjugated π electron system and includes carbocyclic aryl, heterocyclic aryl and biaryl groups. The aryl group may be optionally substituted with one or more substituents including halogen, trihalomethyl, hydroxyl, SH, OH, $NO_2$, $NH_2$, thioether, cyano, alkoxy, alkyl, and amino. Examples of carbocyclic aryl include phenyl, naphthyl, and biphenylenyl.

As used herein, "ester" includes includes both ROCO— (in the case of R=alkyl, alkoxycarbonyl-) and RCOO— (in the case of R=alkyl, alkylcarbonyloxy-).

As used herein, the term "heterocycle" or "heterocyclic ring" refers to a hydrocarbon ring system having a least one heteroatom (such as O, N, or S) as part of the ring in place of one or more carbon atoms. The ring system may or may not be aromatic—that is the ring system may be heteroaryl or heterocyclic. Examples of heteroaryl groups include, but are not limited to furyl, pyrrolyl, pyrazolyl, thiophenyl, thiadiazolyl, tetrazolyl, triazolyl, triazinyl, thienyl, oxazolyl, isoxazolyl, imidazolyl, thiazolyl, isothiazolyl, benzimidazolyl, pyridinyl, pyrimidinyl, quinazolinyl, indolyl, indiazolyl, isoindolyl, benzotriazolyl, purinyl, benzothiazolyl, benzoisothiazolyl, and benzothiadiazolyl. Examples or heterocyclic groups include but are not limited to piperidyl, morpholinyl, pyranyl, dioxanyl, and piperazinyl. The hetrocyclic ring may be substituted or unsubstituted. Examples of substitution groups include alkyl, halogen (F, Cl, Br, I), hydroxy, amino, alkylamino, dialkylamino, thiol, and alkoxy.

The term "acetoxy" refers to the chemical group O(C=O)$CH_3$.

The term "cancer" refers to a pathological diseases associated with the growth of transformed cells, and includes the pathological progression of the disease. Thus the term includes cancers of all stages and of all cellular origin. Cancer cells have the capacity for autonomous growth (an abnormal state or condition characterized by rapidly proliferating cell growth). The term is meant to include all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate cancer, colorectal cancer, cancer of the head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site. In addition, cancer can be associated with a drug resistance phenotype.

The term "epithelial-mesenchymal transition" (or transformation) (EMT) refers to a biological process where epithelial cells detach from their neighboring cells and become solitary migratory cells. Cancer cells from epithelial tumors undergo EMT when they metastasize.

The terms "hydroxyl" and "hydroxy" both refer to an OH group.

In chemical structures where a carbon-carbon double bond exists (olefins), the double bond may be trans (E), or cis (Z).

Antimetastatic Compounds

The present disclosure addresses a need for effective agents that inhibit MET signaling, such as preventing cellular responses to MET activation at points downstream of the MET receptor itself. By inhibiting MET signaling, compounds could be used to directly treat cancers where MET signaling occurs, to prevent or reduce metastatic cellular behavior, whether by MET activation or other causes, or to improve the efficacy of other cancer treatments.

MDCK cells are a well characterized tissue culture model system. MDCK cells express the MET receptor and respond to treatment with Hepatocyte Growth Factor (HGF) by undergoing epithelial-mesenchyme transition in culture. Briefly, cells flatten, detach from their neighbors, and increase their rates of migration and cell division. Thus, MDCK cells respond to HGF by going from an epithelial state where cells are incorporated into a tissue to a mesenchymal state as individual, highly migratory cells.

Formulas I and II

Compounds that inhibit conversion of MDCK cells responding to HGF include those of formulas I and II, and pharmaceutical salts of them.

Compounds disclosed include those of formula I:

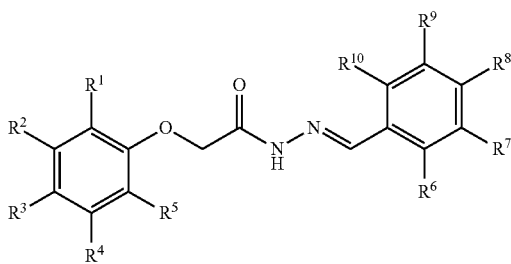

I wherein each of $R^1$, $R^2$, $R^3$, $R^4$, and $R^5$ is selected from the group consisting of: H, alkyl, alkenyl, alkynyl, alkoxy, carboxy, hydroxy, halo, cyano, or together with another R group form a fused ring; wherein each of $R^6$, $R^7$, $R^8$, $R^9$, and $R^{10}$ is selected from the group consisting of: H, alkyl, alkenyl, alkynyl, alkoxy, carboxy, carboxyalkyl, hydroxy, halo, cyano, nitro, or together with another R group form a fused ring; and pharmaceutically acceptable salts thereof.

In some embodiments, two of $R^1$, $R^2$, $R^3$, $R^4$, and $R^5$ together form a fused ring. In some embodiments, $R^1$ and $R^2$ may form a fused ring. In some embodiments, $R^2$ and $R^3$ may form a fused ring. In some embodiments, $R^3$ and $R^4$ may form a fused ring. In some embodiments $R^4$ and $R^5$ may form a fused ring.

In some embodiments, two of $R^6$, $R^7$, $R^8$, $R^9$, and $R^{10}$ together form a fused ring. In some embodiments, $R^6$ and $R^7$ may form a fused ring. In some embodiments, $R^7$ and $R^8$ may form a fused ring. In some embodiments, $R^8$ and $R^9$ may form a fused ring. In some embodiments $R^9$ and $R^{10}$ may form a fused ring.

In some embodiments, $R^1$ is selected from alkyl, alkenyl, alkoxy, and cyano. In some embodiments, $R^1$ is selected from alkyl and alkenyl. In some embodiments, $R^1$ is selected from alkenyl and cyano. In some embodiments, $R^1$ is selected from ethyl, allyl, ethoxy, and cyano. In some embodiments, $R^1$ is selected from alkoxy and cyano. In some embodiments, $R^1$ is selected from alkenyl and alkoxy. In some embodiments, $R^1$ is alkoxy. In some embodiments, $R^1$ is ethoxy. In some embodiments, $R^1$ is methoxy. In some embodiments, $R^1$ is alkenyl. In some embodiments, $R^1$ is allyl. In some embodiments, $R^1$ is cyano. In some embodiments, $R^1$ is alkyl. In some embodiments, $R^1$ is ethyl. In some embodiments, $R^1$ is methyl. In some embodiments, $R^6$ is selected from the group consisting of: alkyl, alkoxy, hydroxy, halo, and H. In some embodiments, $R^6$ is alkyl. In some embodiments, $R^6$ is methyl. In some embodiments, $R^6$ is alkoxy. In some embodiments, $R^6$ is —OCH$_2$CHCH$_2$. In some embodiments, $R^6$ is ethoxy. In some embodiments, $R^6$ is methoxy. In some embodiments, $R^6$ is alkyl. In some embodiments, $R^6$ is hydroxy. In some embodiments, $R^6$ is halo. In some embodiments, $R^6$ is chloro. In some embodiments, $R^6$ is bromo. In some embodiments, $R^6$ is iodo. In some embodiments, $R^6$ is fluoro. In some embodiments, $R^6$ is H.

In some embodiments, $R^7$ is selected from H, alkenyl, alkoxy, halo, and hydroxy. In some embodiments, $R^7$ is H. In some embodiments, $R^7$ is alkenyl. In some embodiments, $R^7$ is allyl. In some embodiments, $R^7$ is alkoxy. In some embodiments, $R^7$ is phenoxy. In some embodiments, $R^7$ is halo. In some embodiments, $R^7$ is iodo. In some embodiments, $R^7$ is bromo. In some embodiments, $R^7$ is chloro. In some embodiments, $R^7$ is fluoro. In some embodiments, $R^7$ is hydroxy.

In some embodiments, $R^8$ is selected from H, alkyl, hydroxy, halo, and nitro. In some embodiments, $R^8$ is H. In some embodiments, $R^8$ is alkyl. In some embodiments, $R^8$ is methyl. In some embodiments, $R^8$ is hydroxy. In some embodiments, $R^8$ is halo. In some embodiments, $R^8$ is iodo. In some embodiments, $R^8$ is bromo. In some embodiments, $R^8$ is chloro. In some embodiments, $R^8$ is fluoro. In some embodiments, $R^8$ is nitro.

In some embodiments, $R^{10}$ is halo. In some embodiments, $R^{10}$ is iodo. In some embodiments, $R^{10}$ is bromo. In some embodiments, $R^{10}$ is chloro. In some embodiments, $R^{10}$ is fluoro.

In some embodiments where an R group (any of $R^1$-$R^{10}$) may be alkoxy, the alkoxy group has 2 to 10 carbon atoms. In some embodiments, the alkoxy group has 2 to 8 carbon atoms. In some embodiments, the alkoxy group has from 2 to 4 carbon atoms.

Compounds disclosed also include those of formula II:

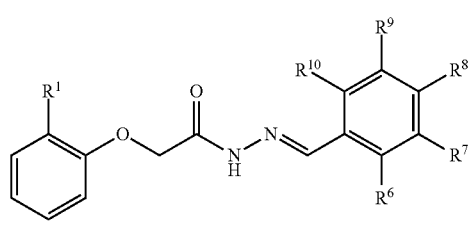

II wherein $R^1$ is selected from alkyl, alkenyl, alkoxy, and cyano; wherein each of $R^6$, $R^7$, $R^8$, $R^9$, and $R^{10}$ is selected from the group consisting of: H, alkyl, alkenyl, alkynyl, alkoxy, carboxy, carboxyalkyl, hydroxy, halo, cyano, nitro, or together with another R group form a fused ring; and pharmaceutically acceptable salts thereof.

In some embodiments, $R^1$ is selected from alkyl, alkenyl, alkoxy, and cyano. In some embodiments, $R^1$ is selected from alkyl and alkenyl. In some embodiments, $R^1$ is selected from alkenyl and cyano. In some embodiments, $R^1$ is selected from ethyl, allyl, ethoxy, and cyano. In some embodiments, $R^1$ is selected from alkoxy and cyano. In some embodiments, $R^1$ is selected from alkenyl and alkoxy. In some embodiments, $R^1$ is alkoxy. In some embodiments, $R^1$ is ethoxy. In some embodiments, $R^1$ is methoxy. In some embodiments, $R^1$ is alkenyl. In some embodiments, $R^1$ is allyl. In some embodiments, $R^1$ is cyano. In some embodiments, $R^1$ is alkyl. In some embodiments, $R^1$ is ethyl. In some embodiments, $R^1$ is methyl.

In some embodiments, $R^6$ is selected from the group consisting of: alkyl, alkoxy, hydroxy, halo, and H. In some embodiments, $R^6$ is alkyl. In some embodiments, $R^6$ is methyl. In some embodiments, $R^6$ is alkoxy. In some embodiments, $R^6$ is —OCH$_2$CHCH$_2$. In some embodiments, $R^6$ is ethoxy. In some embodiments, $R^6$ is methoxy. In some embodiments, $R^6$ is alkyl. In some embodiments, $R^6$ is hydroxy. In some embodiments, $R^6$ is halo. In some embodiments, $R^6$ is chloro. In some embodiments, $R^6$ is bromo. In some embodiments, $R^6$ is iodo. In some embodiments, $R^6$ is fluoro. In some embodiments, $R^6$ is H.

In some embodiments, $R^7$ is selected from H, alkenyl, alkoxy, halo, and hydroxy. In some embodiments, $R^7$ is H. In some embodiments, $R^7$ is alkenyl. In some embodiments, $R^7$ is allyl. In some embodiments, $R^7$ is alkoxy. In some embodiments, $R^7$ is phenoxy. In some embodiments, $R^7$ is halo. In some embodiments, $R^7$ is iodo. In some embodiments, $R^7$ is bromo. In some embodiments, $R^7$ is chloro. In some embodiments, $R^7$ is fluoro.

In some embodiments, $R^8$ is selected from H, alkyl, hydroxy, halo, and nitro. In some embodiments, $R^8$ is H. In some embodiments, $R^8$ is alkyl. In some embodiments, $R^8$ is methyl. In some embodiments, $R^8$ is hydroxy. In some embodiments, $R^8$ is halo. In some embodiments, $R^8$ is iodo. In some embodiments, $R^8$ is bromo. In some embodiments, $R^8$ is chloro. In some embodiments, $R^8$ is fluoro. In some embodiments, $R^8$ is nitro.

In some embodiments, $R^{10}$ is halo. In some embodiments, $R^{10}$ is iodo. In some embodiments, $R^{10}$ is bromo. In some embodiments, $R^{10}$ is chloro. In some embodiments, $R^{10}$ is fluoro.

In some embodiments where an R group ($R^1$, $R^5$-$R^{10}$) may be alkoxy, the alkoxy group has 2 to 10 carbon atoms. In some embodiments, the alkoxy group has 2 to 8 carbon atoms. In some embodiments, the alkoxy group has from 2 to 4 carbon atoms.

The compounds that are capable of inhibiting MET signaling include those of formulas I and II, as further described above.

Illustrative examples of the compounds of Formula I are provided in Table 1.

TABLE 1

| Compound ID | $R^1, R^2, R^3, R^4, R^5$ | $R^6, R^7, R^8, R^9, R^{10}$ | Assay Value |
|---|---|---|---|
| 1 | $R^1$ = allyl; $R^2, R^3, R^4, R^5$ = H | $R^6, R^8$ = methyl; $R^7, R^9, R^{10}$ = H | 97.0 |
| 2 | $R^1$ = allyl; $R^2, R^3, R^4, R^5$ = H | $R^6, R^7, R^9, R^{10}$ = H; $R^8$ = chloro | 67.3 |
| 3 | $R^1$ = allyl; $R^2, R^3, R^4, R^5$ = H | $R^6, R^8, R^9, R^{10}$ = H; $R^7$ = phenoxy | 70.9 |
| 4 | $R^1$ = ethoxy; $R^2, R^3, R^4, R^5$ = H | $R^6, R^8$ = hydroxy; $R^7, R^9, R^{10}$ = H | 32.3 |
| 5 | $R^1$ = cyano; $R^2, R^3, R^4, R^5$ = H | $R^6$ = hydroxy; $R^7, R^8, R^9, R^{10}$ = H | 41.1 |
| 6 | $R^1$ = cyano; $R^2, R^3, R^4, R^5$ = H | $R^6, R^7, R^8, R^9, R^{10}$ = H | 44.2 |
| 7 | $R^1$ = cyano; $R^2, R^3, R^4, R^5$ = H | $R^6, R^7, R^9, R^{10}$ = H; $R^8$ = chloro | 86.8 |
| 8 | $R^1$ = cyano; $R^2, R^3, R^4, R^5$ = H | $R^6, R^8$ = chloro; $R^7, R^9, R^{10}$ = H | 55.1 |
| 9 | $R^1$ = allyl; $R^2, R^3, R^4, R^5$ = H | $R^6$ = OCH$_2$CHCH$_2$; $R^7, R^8, R^9, R^{10}$ = H | 49.5 |
| 10 | $R^1$ = allyl; $R^2, R^3, R^4, R^5$ = H | $R^6$ = hydroxyl; $R^7$ = allyl; $R^8, R^9, R^{10}$ = H | 44.8 |
| 11 | $R^1$ = cyano; $R^2, R^3, R^4, R^5$ = H | $R^8$ = nitro; $R^6, R^7, R^9, R^{10}$ = H | 83.7 |
| 12 | $R^1$ = cyano; $R^2, R^3, R^4, R^5$ = H | $R^6, R^8, R^9, R^{10}$ = H; $R^7$ = bromo | 67.7 |
| 13 | $R^1$ = cyano; $R^2, R^3, R^4, R^5$ = H | $R^6, R^{10}$ = chloro; $R^7, R^8, R^9$ = H | 86.0 |
| 14 | $R^1$ = ethyl; $R^2, R^3, R^4, R^5$ = H | $R^8$ = bromo; $R^6, R^7, R^9, R^{10}$ = H | 100 |
| 15 | $R^1$ = ethoxy; $R^2, R^3, R^4, R^5$ = H | $R^7, R^8$ = OH; $R^6, R^9, R^{10}$ = H | 72.8 |
| 16 | $R^2$ = methyl; $R^1, R^3, R^4, R^5$ = H | $R^7$ = iodo; $R^6, R^8, R^9, R^{10}$ = H | <5 |
| 17 | $R^1, R^3, R^5$ = methyl; $R^2, R^4$ = H | $R^6, R^7, R^8, R^9, R^{10}$ = H | <5 |
| 18 | $R^1, R^3, R^5$ = methyl; $R^2, R^4$ = H | $R^6$ = methoxy; $R^7, R^8, R^9, R^{10}$ = H | <5 |
| 19 | R1 = methyl; $R^2, R^3, R^4, R^5$ = H | $R^8$ = methoxy; $R^6, R^7, R^9, R^{10}$ = H | <5 |
| 20 | $R^3$ = methyl; $R^1, R^2, R^4, R^5$ = H | $R^6, R^7, R^8, R^9, R^{10}$ = H | <5 |
| 21 | $R^1, R^2, R^3, R^4, R^5$ = H | $R^6, R^8, R^{10}$ = methyl; $R^7, R^9$ = H | <5 |
| 22 | $R^1$, Rb = methyl; $R^2, R^4, R^5$ = H | $R^8$ = carboxy; $R^6, R^7, R^9, R^{10}$ = H | <5 |
| 23 | $R^1, R^2$ = methyl; $R^3, R^4, R^5$ = H | $R^8$ = hydroxyl; $R^6, R^7, R^9, R^{10}$ = H | <5 |
| 24 | $R^1$ = isopropyl; $R^4$ = methyl; $R^2, R^3, R^5$ = H | $R^7$ = methoxy; $R^6, R^8, R^9, R^{10}$ = H | <5 |
| 25 | $R^1, R^2, R^5$ = methyl; $R^3, R^4$ = H | $R^8$ = carboxymethyl; $R^6, R^7, R^9, R^{10}$ = H | <5 |
| 26 | $R^1$ = methyl; $R^2, R^3, R^4, R^5$ = H | $R^8$ = fluoro; $R^6, R^7, R^9, R^{10}$ = H | <5 |
| 27 | $R^1$ = methoxy; $R^2, R^3, R^4, R^5$ = H | $R^6$ = hydroxy; $R^7$ = allyl; $R^8, R^9, R^{10}$ = H | <5 |
| 28 | $R^1$ = bromo; $R^2, R^3, R^4, R^5$ = H | $R^7$ = bromo; $R^6, R^8, R^9, R^{10}$ = H | <5 |
| 29 | $R^1$ = methoxy; $R^2, R^3, R^4, R^5$ = H | $R^6, R^7$ = fused phenyl; $R^9, R^{10}$ = fused phenyl; $R^8$ = H | <5 |
| 30 | $R^2, R^3$ = fused phenyl; $R^1, R^4, R^5$ = H | $R^6$ = bromo; $R^7, R^8, R^9, R^{10}$ = H | <5 |
| 31 | $R^2, R^3$ = fused phenyl; $R^1, R^4, R^5$ = H | $R^6, R^7, R^8, R^9, R^{10}$ = H | <5 |

TABLE 1-continued

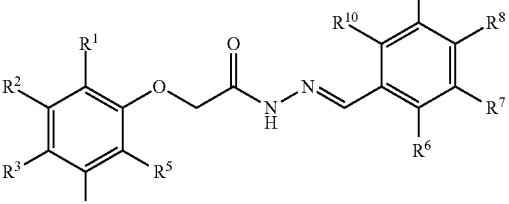

| Compound ID | $R^1, R^2, R^3, R^4, R^5$ | $R^6, R^7, R^8, R^9, R^{10}$ | Assay Value |
|---|---|---|---|
| 32 | $R^1$ = methoxy; $R^2, R^3, R^4, R^5$ = H | $R^6$ = methoxy; $R^7, R^8, R^9, R^{10}$ = H | <5 |
| 33 | $R^1$ = methoxy; $R^2, R^3, R^4, R^5$ = H | $R^8$ = chloro; $R^6, R^7, R^9, R^{10}$ = H | <5 |
| 34 | $R^1$ = bromo; $R^2, R^3, R^4, R^5$ = H | $R^6, R^8$ = methyl; $R^7, R^9, R^{10}$ = H | <5 |
| 35 | $R^2$ = bromo; $R^1, R^3, R^4, R^5$ = H | $R^8$ = chloro; $R^6, R^7, R^9, R^{10}$ = H | <5 |
| 36 | $R^2$ = bromo; $R^1, R^3, R^4, R^5$ = H | $R^6, R^8$ = methyl; $R^7, R^9, R^{10}$ = H | <5 |
| 37 | $R^1$ = bromo; $R^2, R^3, R^4, R^5$ = H | $R^6$ = bromo; $R^7, R^8, R^9, R^{10}$ = H | <5 |
| 38 | $R^3$ = bromo; $R^2, R^3, R^4, R^5$ = H | $R^8$ = chloro; $R^6, R^7, R^9, R^{10}$ = H | <5 |

Compounds 1 through 15 are also depicted below:

1
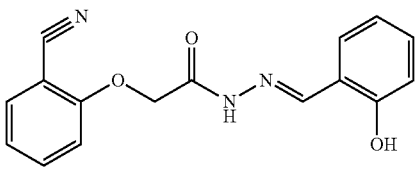

2
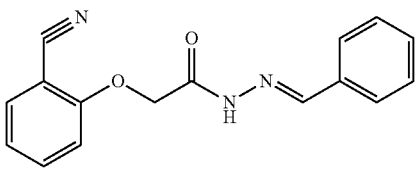

3
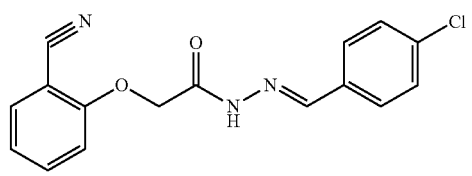

4
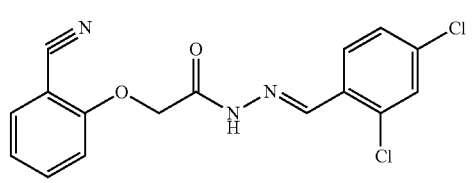

5
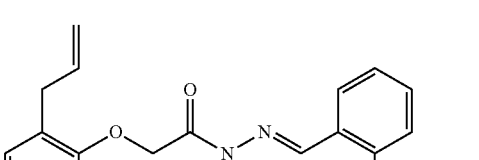

6
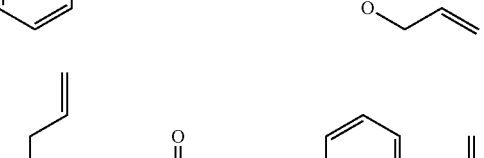

7
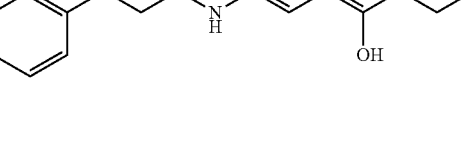

8
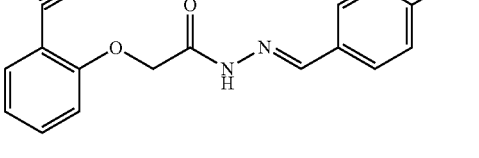

9
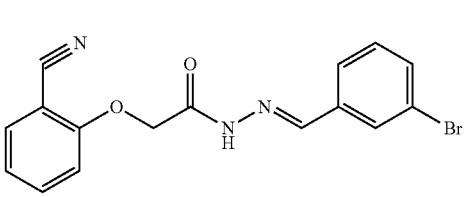

-continued

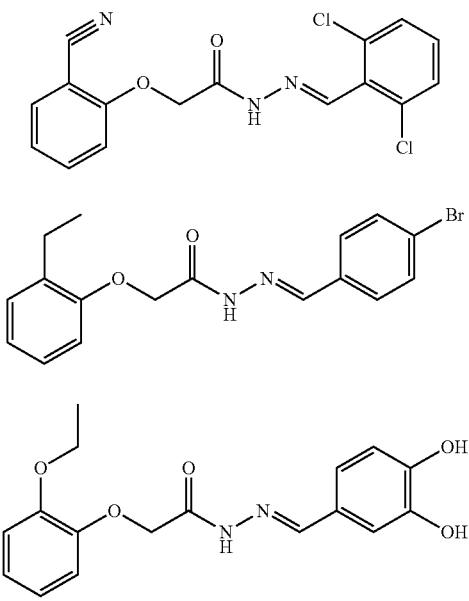

Illustrative examples of the compounds of Formula II are provided in Table 2.

TABLE 2

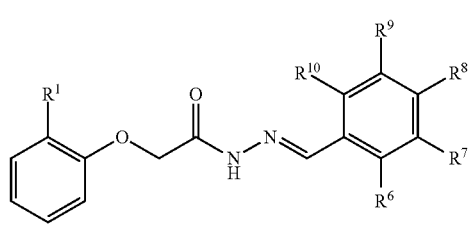

| Compound ID | R$^1$ | R$^6$ | R$^7$ | R$^8$ | R$^9$ | R$^{10}$ | Assay Value |
|---|---|---|---|---|---|---|---|
| 1 | allyl | methyl | H | methyl | H | H | 97.0 |
| 2 | allyl | H | H | chloro | H | H | 67.3 |
| 3 | allyl | H | phenoxy | H | H | H | 70.9 |
| 4 | ethoxy | hydroxy | H | hydroxyl | H | H | 32.3 |
| 5 | cyano | hydroxy | H | H | H | H | 41.1 |
| 6 | cyano | H | H | H | H | H | 44.2 |
| 7 | cyano | H | H | chloro | H | H | 86.8 |
| 8 | cyano | chloro | H | chloro | H | H | 55.1 |
| 9 | allyl | OCH$_2$CHCH$_2$ | H | H | H | H | 49.5 |
| 10 | allyl | hydroxy | allyl | H | H | H | 44.8 |
| 11 | cyano | H | H | nitro | H | H | 83.7 |
| 12 | cyano | H | bromo | H | H | H | 67.7 |
| 13 | cyano | chloro | H | H | H | Cl | 86.0 |
| 14 | ethyl | H | H | Br | H | H | 100 |
| 15 | ethoxy | H | OH | OH | H | H | 72.8 |
| 27 | methoxy | hydroxyl | allyl | H | H | H | <5 |
| 29 | methoxy | fused phenyl | | H | fused phenyl | | <5 |
| 32 | methoxy | methoxy | H | H | H | H | <5 |

Compounds I-38 are available from Chembridge Corporation, 16981 Via Tazon, Suite G, San Diego, Calif. 92127.

Formulas A-I, A-II, A-IIa, A-IIb, A-III, and A-IV

Compounds that inhibit conversion of MDCK cells responding to HGF include those of formulas A-I, A-II, A-IIa, A-IIb, A-III, and A-IV, and pharmaceutical salts of them.

Compounds disclosed include those of formula A-I:

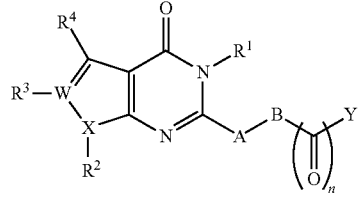

A-I wherein R$^1$ is selected from H, phenyl, and benzyl; R$^2$ is absent or H; R$^3$ is H, absent, or together with R$^4$ forms a carbocyclic ring; R$^4$ is H, absent or together with R$^3$ forms a carbocyclic ring; X is N, S, or together with W completes a phenyl ring; W is C, N, or together with X completes a phenyl ring; A is absent or selected from S and NH; B is absent or selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

In some embodiments, R$^1$ is H. In some embodiments, R$^1$ is phenyl. In some embodiments, R$^1$ is benzyl. In some embodiments, R$^1$ is selected from phenyl and benzyl.

In some embodiments, R$^2$ is H. In some embodiments, R$^2$ is absent.

In some embodiments, R$^3$ is H. In some embodiments, R$^3$ is absent. In some embodiments, R$^3$ forms a carbocyclic ring with R$^4$.

In some embodiments, R$^4$ is H. In some embodiments, R$^4$ is absent. In some embodiments, R$^4$ forms a carbocyclic ring with R$^3$.

In some embodiments, X is N. In some embodiments, X is S. In some embodiments, X completes a phenyl ring with W.

In some embodiments, W is C. In some embodiments, W is S. In some embodiments, W completes a phenyl ring with X.

In some embodiments, A is absent. In some embodiments, A is S. In some embodiments, A is NH.

In some embodiments, B is absent. In some embodiments, B is alkyl.

In some embodiments, B is CH$_2$. In some embodiments, B is CH$_2$—CH$_2$—CH$_2$.

In some embodiments, B is alkenyl. In some embodiments, B is CH$_2$—CH=CH.

In some embodiments, n is 0. In some embodiments, n is 1.

In some embodiments, Y is selected from alkyl, alkenyl, alkoxy, and hydroxy. In some embodiments, Y is alkyl. In some embodiments, Y is methyl. In some embodiments, Y is ethyl. In some embodiments, Y is alkenyl. In some embodiments, Y is —(C=CH$_2$)—CH$_3$. In some embodiments, Y is alkoxy. In some embodiments, Y is ethoxy. In some embodiments, Y is methoxy. In some embodiments, Y is hydroxy.

Compounds disclosed also include those of formula A-II:

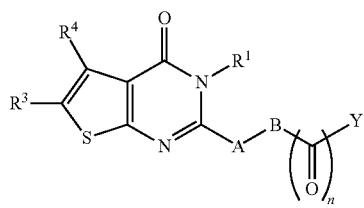

A-II wherein $R^1$ is selected from H, phenyl, and benzyl; $R^3$ is H or together with $R^4$ forms a carbocyclic ring; $R^4$ is H or together with $R^3$ forms a carbocyclic ring; A is absent or selected from S and NH; B absent or is selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

Compounds disclosed also include those of formula A-IIa and A-IIb:

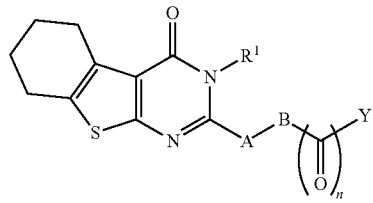

A-IIa

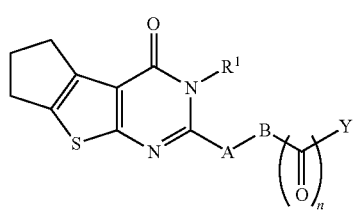

A-IIb wherein $R^1$ is selected from H, phenyl, and benzyl; n is 0 or 1; A is absent or selected from S and NH; B absent or is selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

Compounds disclosed also include those of formula A-III:

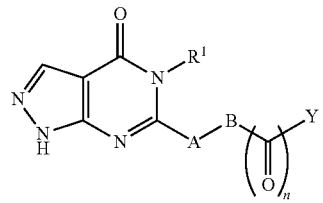

A-III wherein $R^1$ is selected from H, phenyl, and benzyl; A is absent or selected from S and NH; B is absent or selected from alkyl and alkenyl; n is 0 or 1; Y is selected from alkyl, alkenyl, alkoxy, hydroxy, unsubstituted aryl, unsubstituted heteroaryl, substituted aryl, and substituted heteroaryl; and pharmaceutically acceptable salts thereof.

Compounds disclosed also include those of formula A-IV:

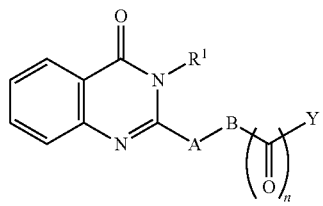

A-IV wherein $R^1$ is selected from H, phenyl, and benzyl; A is absent or selected from S and NH; B absent or is selected from alkyl and alkenyl; n is 0 or 1; Y is selected from alkyl, alkenyl, alkoxy, hydroxy, unsubstituted aryl, substituted aryl, and heterocycle; and pharmaceutically acceptable salts thereof.

The compounds that are capable of inhibiting MET signaling include those of formulas A-I, A-II, A-IIa, A-IIb, A-III, and A-IV, as further described above.

Illustrative examples of the compounds of Formula A-I are provided in Table 3.

TABLE 3

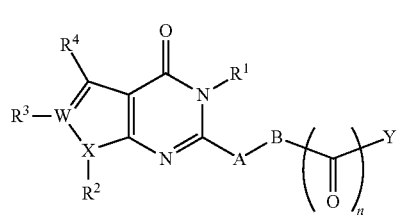

A-I

| Compound No. | $R^1$ | $R^2$ | $R^3$ | $R^4$ | W | X | A-B | n | Y | Assay Value |
|---|---|---|---|---|---|---|---|---|---|---|
| A-1 | H | | —CH$_2$CH$_2$CH$_2$CH$_2$— | | C | S | CH$_2$—CH$_2$ | 0 | phenyl | 96.9 |
| A-2 | H | | —CH$_2$CH$_2$CH$_2$CH$_2$— | | C | S | NH—CH$_2$ | 0 | phenyl | 92.2 |
| A-3 | H | | —CH$_2$CH$_2$CH$_2$CH$_2$— | | C | S | CH$_2$—CH$_2$ | 0 | 1H-benzo[de]-isoquinoline-1,3(2H)-dionyl | 73.4 |
| A-4 | H | | —CH$_2$CH$_2$CH$_2$CH$_2$— | | C | S | CH=CH | 0 | phenyl | 90.8 |

TABLE 3-continued

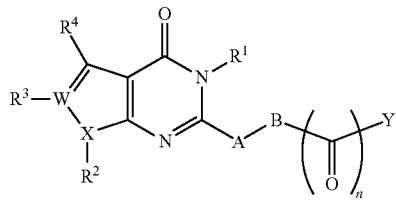

A-I

| Compound No. | R¹ | R² | R³ | R⁴ | W | X | A-B | n | Y | Assay Value |
|---|---|---|---|---|---|---|---|---|---|---|
| A-5 | H | | \[fused tetrahydroquinoline\] | | C | S | S—CH$_2$ | 0 | phenyl | 77.3 |
| A-6 | phenyl | | —CH$_2$CH$_2$CH$_2$— | | C | S | S—CH$_2$ | 0 | 3,5-dimethyl-isoxazole | 55.1 |
| A-7 | phenyl | | —CH$_2$CH$_2$CH$_2$CH$_2$— | | C | S | S—CH$_2$ | 0 | 3,5-dimethyl-isoxazole | 31.3 |
| A-8 | phenyl | H | | H | N | N | S—CH$_2$ | 0 | 2-methyl-thiazol-4-yl | 49.6 |
| A-9 | benzyl | | —CH$_2$CH$_2$CH$_2$CH$_2$— | | C | S | S—CH$_2$ | 1 | pyrrolidin-1-yl | 50.0 |
| A-10 | phenyl | H | | H | N | N | S—CH$_2$ | 0 | 3,5-dimethyl-isoxazol-4-yl | 63.1 |
| A-11 | H | H | H | H | phenyl ring | | | 0 | phenyl | 88.0 |
| A-12 | H | | —CH$_2$CH$_2$CH$_2$CH$_2$— | | C | S | CH$_2$—CH$_2$ | 1 | OH | 100 |
| A-13 | H | | —CH$_2$CH$_2$CH$_2$CH$_2$— | | C | S | S—CH$_2$—CH=CH | 0 | phenyl | 90.5 |
| A-14 | H | | —CH$_2$CH$_2$CH$_2$CH$_2$— | | C | S | S—CH$_2$ | 0 | \[isopropenyl\] | 100 |
| A-15 | H | | —CH$_2$CH$_2$CH$_2$CH$_2$— | | C | S | S—CH$_2$—CH=CH | 1 | —OCH$_2$—CH$_3$ | 71.3 |
| A-16 | H | | —CH$_2$CH$_2$CH$_2$CH$_2$— | | C | S | CH$_2$—CH$_2$—CH$_2$ | 0 | 1H-benzo[de]-isoquinoline-1,3(2H)-dionyl | 70.1 |
| A-17 | phenyl | | —CH$_2$CH$_2$CH$_2$CH$_2$— | | C | S | S—CH$_2$ | 1 | thiophen-2-yl | <5 |
| A-18 | H | | \[methyl-tetrahydropyridine\] | | C | S | CH$_2$ | 0 | phenyl | <5 |
| A-19 | H | | fused 2,2-dimethyl-3,6-dihydro-2H-pyran | | C | S | NH | 0 | phenyl | <5 |
| A-20 | benzyl | | \[methyl-tetrahydropyridine\] | | C | S | S—CH$_2$ | 1 | morpholin-4-yl | <5 |
| A-21 | benzyl | | —CH$_2$CH$_2$CH$_2$CH$_2$— | | C | S | S—CH$_2$ | 1 | pyrrolidin-1-yl | <5 |
| A-22 | phenyl | | —CH$_2$CH$_2$CH$_2$— | | C | S | S—CH$_2$ | 1 | 2-methyl-piperin-1-yl | <5 |
| A-23 | H | | —CH$_2$CH$_2$CH$_2$CH$_2$— | | C | S | | 0 | chromen-4-one-3-yl | <5 |

TABLE 3-continued
A-I
| Compound No. | R¹ | R² | R³ | R⁴ | W | X | A-B | n | Y | Assay Value |
|---|---|---|---|---|---|---|---|---|---|---|
| A-24 | H | | fused 2,2-dimethyl-3,6-dihydro-2H-pyran | | C | S | CH₂CH₂ | 0 | phenyl | <5 |
| A-25 | H | | —CH₂CH₂CH₂CH₂— | | C | S | S—CH₂ | 1 | 4-methyl-piperdin-1-yl | <5 |
Compounds A-1 through A-16 are also depicted below:
A-1
A-2
A-3
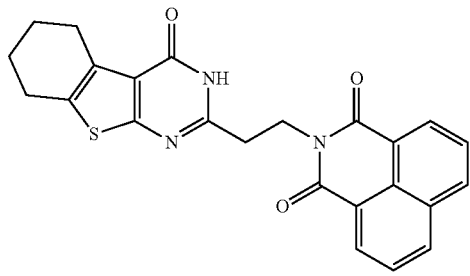
A-4
A-5
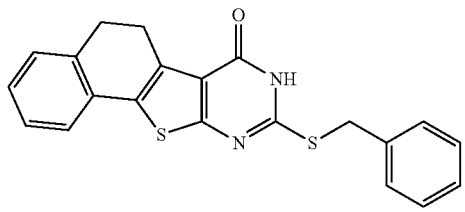
A-6
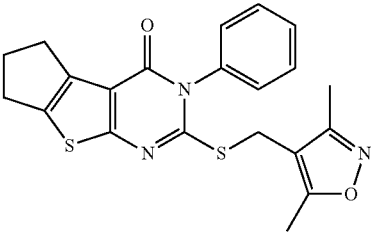
A-7
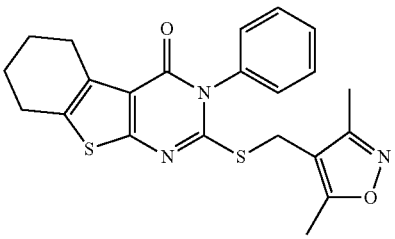
A-8
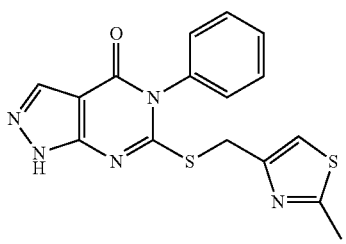

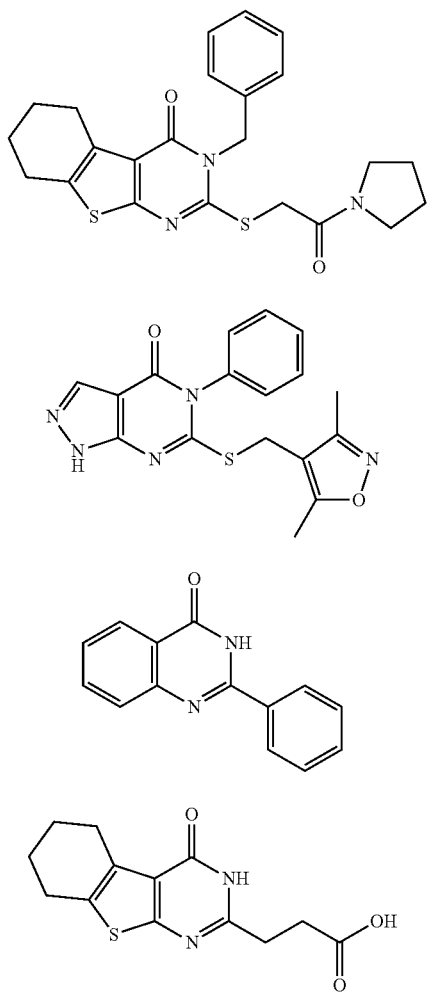

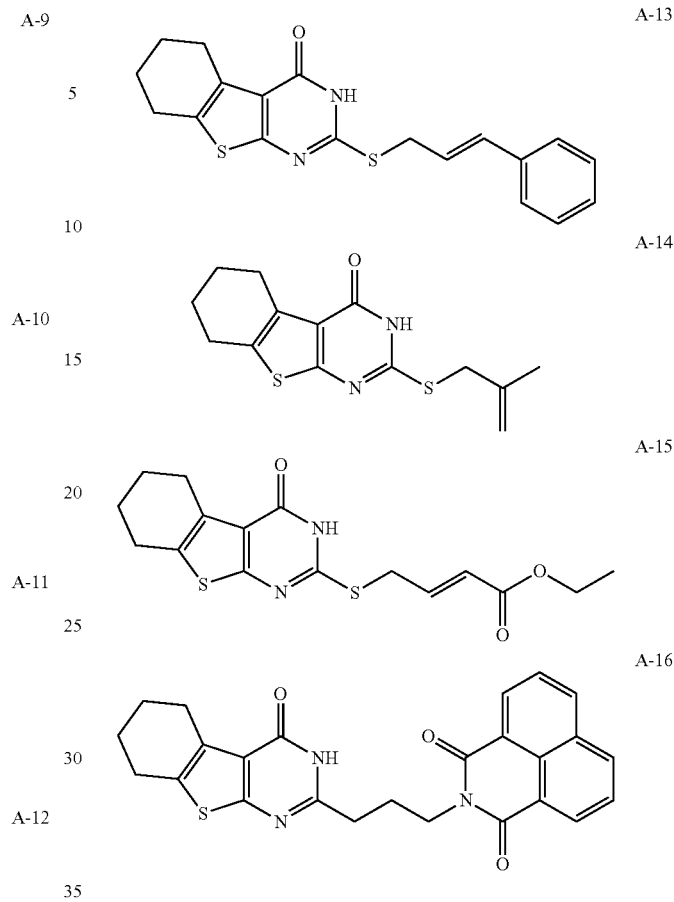

Thus, in some embodiments, a medicinal agent is selected from any one or more of the aforementioned A-1 through A-16 compounds.

Illustrative examples of the compounds of Formula A-II are provided in Table 4.

TABLE 4

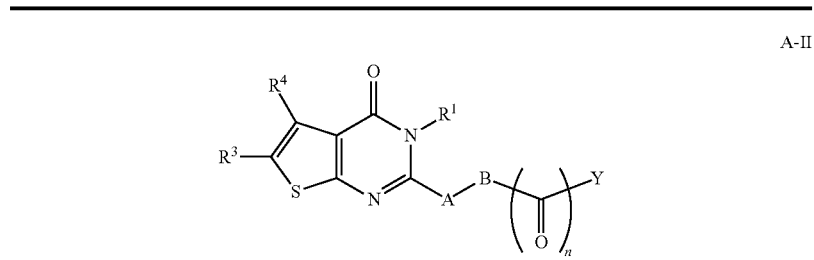

| Compound No. | $R^1$ | $R^3$ | $R^4$ | A-B | n | Y | Assay Value |
|---|---|---|---|---|---|---|---|
| A-1 | H | —CH$_2$CH$_2$CH$_2$CH$_2$— | | CH$_2$—CH$_2$ | 0 | phenyl | 96.9 |
| A-2 | H | —CH$_2$CH$_2$CH$_2$CH$_2$— | | NH—CH$_2$ | 0 | phenyl | 92.2 |
| A-3 | H | —CH$_2$CH$_2$CH$_2$CH$_2$— | | CH$_2$—CH$_2$ | 0 | 1H-benzo[de]-isoquinoline-1,3(2H)-dionyl | 73.4 |
| A-4 | H | —CH$_2$CH$_2$CH$_2$CH$_2$— | | CH=CH | 0 | phenyl | 90.8 |

TABLE 4-continued

A-II

[Structure: thieno[2,3-d]pyrimidinone with R³, R⁴ on thiophene, R¹ on N, and substituent -A-B-(CH(O))ₙ-Y]

| Compound No. | R¹ | R³ | R⁴ | A—B | n | Y | Assay Value |
|---|---|---|---|---|---|---|---|
| A-5 | H | \[fused tetrahydroquinoline with W\] | | S—CH₂ | 0 | phenyl | 77.3 |
| A-6 | phenyl | —CH₂CH₂CH₂— | | S—CH₂ | 0 | 3,5-dimethyl-isoxazole | 55.1 |
| A-7 | phenyl | —CH₂CH₂CH₂CH₂— | | S—CH₂ | 0 | 3,5-dimethyl-isoxazole | 31.3 |
| A-9 | benzyl | —CH₂CH₂CH₂CH₂— | | S—CH₂ | 1 | pyrrolidin-1-yl | 50.0 |
| A-12 | H | —CH₂CH₂CH₂CH₂— | | CH₂—CH₂ | 1 | OH | 100 |
| A-13 | H | —CH₂CH₂CH₂CH₂— | | S—CH₂—CH=CH | 0 | phenyl | 90.5 |
| A-14 | H | —CH₂CH₂CH₂CH₂— | | S—CH₂ | 0 | \[isopropenyl group\] | 100 |
| A-15 | H | —CH₂CH₂CH₂CH₂— | | S—CH₂—CH=CH | 1 | —OCH₂—CH₃ | 71.3 |
| A-16 | H | —CH₂CH₂CH₂CH₂— | | CH₂—CH₂—CH₂ | 0 | 1H-benzo[de]-isoquinoline-1,3(2H)-dionyl | 70.1 |
| A-17 | phenyl | —CH₂CH₂CH₂CH₂— | | S—CH₂ | 1 | thiophen-2-yl | <5 |
| A-18 | H | \[methylpiperidine with W\] | | CH₂ | 0 | phenyl | <5 |
| A-19 | H | fused 2,2-dimethyl-3,6-dihydro-2H-pyran | | NH | 0 | phenyl | <5 |
| A-20 | benzyl | \[methylpiperidine with W\] | | S—CH₂ | 1 | morpholin-4-yl | <5 |
| A-21 | benzyl | —CH₂CH₂CH₂CH₂— | | S—CH₂ | 1 | pyrrolidin-1-yl | <5 |
| A-22 | phenyl | —CH₂CH₂CH₂— | | S—CH₂ | 1 | 2-methyl-piperin-1-yl | <5 |
| A-23 | H | —CH₂CH₂CH₂CH₂— | | | 0 | chromen-4-one-3-yl | <5 |
| A-24 | H | fused 2,2-dimethyl-3,6-dihydro-2H-pyran | | CH₂CH₂ | 0 | phenyl | <5 |
| A-25 | H | —CH₂CH₂CH₂CH₂— | | S—CH₂ | 1 | 4-methyl-piperdin-1-yl | <5 |

Illustrative examples of the compounds of Formula A-IIa are provided in Table 5.

TABLE 5

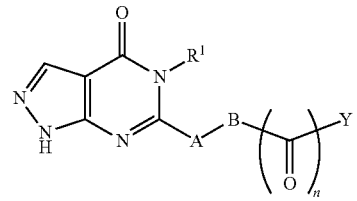

A-IIa

| Compound No. | R¹ | A-B | n | Y | Assay Value |
|---|---|---|---|---|---|
| A-1 | H | $CH_2$—$CH_2$ | 0 | phenyl | 96.9 |
| A-2 | H | NH—$CH_2$ | 0 | phenyl | 92.2 |
| A-3 | H | $CH_2$—$CH_2$ | 0 | 1H-benzo[de]-isoquinoline-1,3(2H)-dionyl | 73.4 |
| A-4 | H | CH=CH | 0 | phenyl | 90.8 |
| A-7 | phenyl | S—$CH_2$ | 0 | 3,5-dimethyl-isoxazole | 31.3 |
| A-9 | benzyl | S—$CH_2$ | 1 | pyrrolidin-1-yl | 50.0 |
| A-12 | H | $CH_2$—$CH_2$ | 1 | OH | 100 |
| A-13 | H | S—$CH_2$—CH=CH | 0 | phenyl | 90.5 |
| A-14 | H | S—$CH_2$ | 0 | (isobutenyl) | 100 |
| A-15 | H | S—$CH_2$—CH=CH | 1 | —$OCH_2$—$CH_3$ | 71.3 |
| A-16 | H | $CH_2$—$CH_2$—$CH_2$ | 0 | 1H-benzo[de]-isoquinoline-1,3(2H)-dionyl | 70.1 |
| A-17 | phenyl | S—$CH_2$ | 1 | thiophen-2-yl | <5 |
| A-19 | benzyl | S—$CH_2$ | 0 | pyrrolidin-1-yl | <5 |
| A-21 | phenyl | S—$CH_2$ | 1 | 2-methyl-piperin-1-yl | <5 |
| A-23 | H | | 0 | chromen-4-one-3-yl | <5 |
| A-25 | H | S—$CH_2$ | 1 | 4-methyl-piperdin-1-yl | <5 |

Illustrative examples of the compounds of Formula A-IIb are provided in Table 6.

TABLE 6

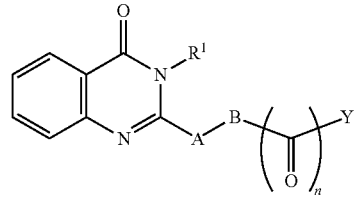

A-IIb

| Compound No. | R¹ | R³ | R⁴ | A-B | n | Y | Assay Value |
|---|---|---|---|---|---|---|---|
| A-6 | phenyl | fused cyclopentene | | S—$CH_2$ | 0 | 3,5-dimethyl-isoxazole | 55.1 |
| A-17 | phenyl | fused cyclopentene | | S—$CH_2$ | 1 | 2-methyl-piperin-1-yl | <5 |

Illustrative examples of the compounds of Formula A-III are provided in Table 7.

TABLE 7

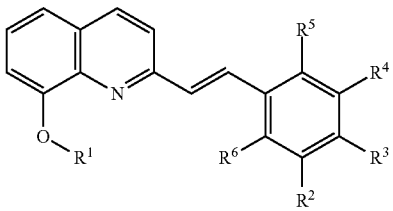

A-III

| Compound No. | R¹ | A-B | n | Y | Assay Value |
|---|---|---|---|---|---|
| A-8 | phenyl | S—$CH_2$ | 0 | 2-methyl-thiazol-4-yl | 49.6 |
| A-10 | phenyl | S—$CH_2$ | 0 | 3,5-dimethyl-isoxazol-4-yl | 63.1 |

Illustrative examples of the compounds of Formula A-IV are provided in Table 8.

TABLE 8

A-IV

| Compound No. | R¹ | A-B | n | Y | Assay Value |
|---|---|---|---|---|---|
| A-11 | H | | 0 | phenyl | 88.0 |

Compounds A-1 through A-25 are available from Chembridge Corporation, 16981 Via Tazon, Suite G, San Diego, Calif. 92127.

Formulas B-I, B-IIa, and B-IIb

Compounds that inhibit conversion of MDCK cells responding to HGF include those of formulas B-I, B-IIa, and B-IIb and pharmaceutical salts of them.

Compounds disclosed include those of formula B-I:

B-I wherein R¹ is selected from H, alkyl, (C=O)alkyl, and optionally substituted benzyl; R² is selected form H, alkyl, halogen, hydroxyl, alkoxy, ester, nitro, and benzyl ether or with R³ forms a heterocyclic ring; R³ is selected form H, alkyl, halogen, hydroxyl, alkoxy, ester, nitro, and benzyl ether or with one of R² and R⁴ forms a heterocyclic ring; R⁴ is selected form H, alkyl, halogen, hydroxyl, alkoxy, ester, and nitro, benzyl ether or with R³ forms a heterocyclic ring; R⁵ is selected form H, alkyl, halogen, hydroxyl, alkoxy, ester, nitro, and benzyl ether; R⁶ is selected form H, alkyl, halogen, hydroxyl, alkoxy, ester, nitro, and benzyl ether; and pharmaceutically acceptable salts thereof.

In some embodiments, $R^1$ is selected from alkyl, (C═O) alkyl, and optionally substituted benzyl. In some embodiments, $R^1$ is acetyl ((C═O)CH$_3$). In some embodiments, $R^1$ is (C═O)CH$_2$CH$_3$. In some embodiments, $R^1$ is 4-chlorobenzyl. In some embodiments, $R^1$ is 3-chlorobenzyl. In some embodiments, $R^1$ is 2-chlorobenzyl. In some embodiments, $R^1$ is benzyl. In some embodiments with compounds of Formula B-I, $R^1$ is alkyl. In some embodiments, $R^1$ is methyl. In some embodiments, $R^1$ is ethyl.

In some embodiments, $R^1$ is H.

In some embodiments, the compound

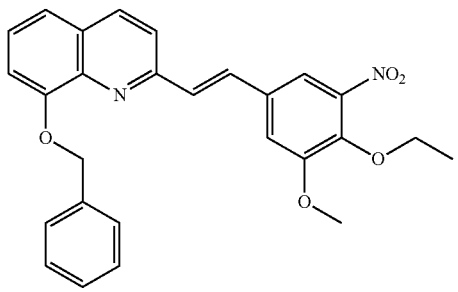 [SMILES: CCOc1c(OC)cc(/C=C/c2ccc3cccc(OCc4ccccc4)c3n2)cc1[N+](=O)[O-]]

is excluded.

Compounds disclosed also include those of formula B-IIa:

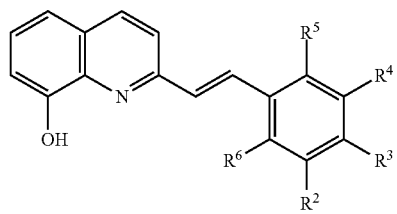

B-IIa wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester nitro, and benzyl ether; $R^6$ is selected form H, alkyl, halogen, hydroxyl, alkoxy, ester, and benzyl ether; and pharmaceutically acceptable salts thereof.

Compounds disclosed also include those of formula B-IIb:

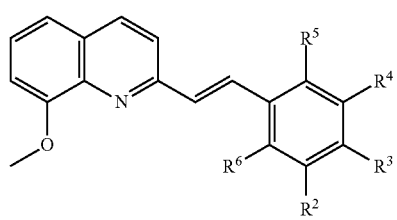

B-IIb wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; and pharmaceutically acceptable salts thereof.

Compounds disclosed also include those of formula B-IIc:

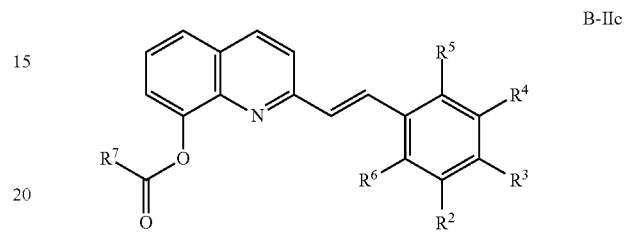

B-IIc wherein $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; $R^7$ is alkyl; and pharmaceutically acceptable salts thereof.

Compounds disclosed also include those of formula B-IId:

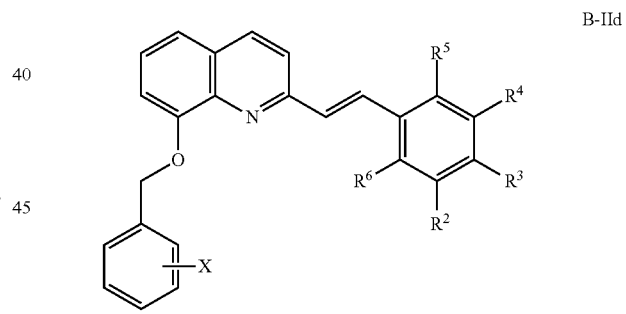

B-IId wherein X is halogen or absent; $R^2$ is selected form H, alkyl, halogen, hydroxyl, alkoxy, ester, nitro, and benzyl ether or with $R^3$ forms a heterocyclic ring; $R^3$ is selected form H, alkyl, halogen, hydroxyl, alkoxy, ester, nitro, and benzyl ether or with one of $R^2$ and $R^4$ forms a heterocyclic ring; $R^4$ is selected form H, alkyl, halogen, hydroxyl, alkoxy, ester, nitro, and benzyl ether or with $R^3$ forms a heterocyclic ring; $R^5$ is selected form H, alkyl, halogen, hydroxyl, alkoxy, ester, nitro, and benzyl ether; $R^6$ is selected form H, alkyl, halogen, hydroxyl, alkoxy, ester, nitro, and benzyl ether; and pharmaceutically acceptable salts thereof.

In some embodiments, X is chloro. In some embodiments, X is bromo. In some embodiments, X is iodo. In some embodiments, X is fluoro.

In some embodiments with compounds of Formulas B-I, B-IIa, B-IIb, B-IIc, and B-IId, $R^4$ is H. In some embodiments, $R^4$ is methoxy.

In some embodiments with compounds of Formulas B-I, B-IIa, B-IIb, B-IIc, and B-IId, $R^2$ is selected from H, ethoxy, methoxy, chloro, and bromo; $R^3$ is selected from H, methoxy, ethoxy, hydroxyl, acetyl, and chloro.

In some embodiments with compounds of Formulas B-I, B-IIa, B-IIb, B-IIc, and B-IId, $R^2$ is selected from H, ethoxy methoxy, chloro, bromo, nitro, and acetoxy; $R^3$ is selected from methoxy, ethoxy, hydroxyl, acetyl, and chloro.

In some embodiments with compounds of Formulas B-I, B-IIa, B-IIb, B-IIc, and B-IId, $R^2$ is methoxy. In some embodiments, $R^2$ is ethoxy. In some embodiments, $R^2$ is chloro. In some embodiments, $R^2$ is bromo. In some embodiments, $R^2$ is iodo. In some embodiments, $R^2$ is bromo. In some embodiments, $R^2$ is H. In some embodiments, $R^2$ is nitro. In some embodiments, $R^2$ is acetoxy.

In some embodiments with compounds of Formulas B-I, B-IIa, B-IIb, B-IIc, and B-IId, $R^3$ is methoxy. In some embodiments, $R^3$ is ethoxy. In some embodiments, $R^3$ is O-carbocycle. In some embodiments, $R^3$ is O-cyclopentyl. In some embodiments, $R^3$ is O-benzyl. In some embodiments, $R^3$ is $O(C=O)CH_2CH_3$. In some embodiments, $R^3$ is hydroxyl. In some embodiments, $R^3$ is acetyl. In some embodiments, $R^3$ is acetoxy. In some embodiments, $R^3$ is alkyl. In some embodiments, $R^3$ is methyl. In some embodiments, $R^3$ is ethyl. In some embodiments, $R^3$ is propyl. In some embodiments, $R^3$ is n-propyl. In some embodiments, $R^3$ is iso-propyl. In some embodiments, $R^3$ is chloro. In some embodiments, $R^3$ is bromo. In some embodiments, $R^3$ is H.

In some embodiments, $R^2$ and $R^3$ form a heterocyclic ring. In some embodiments, $R^2$ and $R^3$ form a 1,3-dioxole ring. In some embodiments, $R^3$ and $R^4$ form a heterocyclic ring. In some embodiments, $R^3$ and $R^4$ form a 1,3-dioxole ring.

In some embodiments with compounds of Formulas B-I, B-IIa, B-IIb, B-IIc, and B-IId, $R^4$ is methoxy. In some embodiments, $R^4$ is ethoxy. In some embodiments, $R^4$ is chloro. In some embodiments, $R^4$ is bromo. In some embodiments, $R^4$ is iodo. In some embodiments, $R^4$ is H. In some embodiments, $R^4$ is nitro. In some embodiments, $R^4$ is acetoxy.

In some embodiments with compounds of Formulas B-I, B-IIa, B-IIb, B-IIc, and B-IId, $R^5$ is methoxy. In some embodiments, $R^5$ is ethoxy. In some embodiments, $R^5$ is nitro. In some embodiments, $R^5$ is acetoxy. In some embodiments, $R^5$ is hydroxy. In some embodiments, $R^5$ is hydroxy. In some embodiments, $R^5$ is H.

In some embodiments with compounds of Formulas B-I, B-IIa, B-IIb, B-IIc, and B-IId, $R^6$ is methoxy. In some embodiments, $R^6$ is nitro. In some embodiments, $R^6$ is acetoxy.

The compounds that are capable of inhibiting MET signaling include those of Formulas B-I, B-IIa, B-IIb, B-IIc, and B-IId as further described above.

Illustrative examples of the compounds of Formula B-1 are provided in Table 9.

TABLE 9

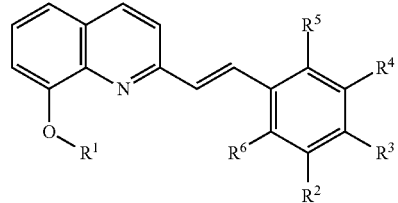

B-I

| Compound No. | $R^1$ | $R^2$ | $R^3$ | $R^4$ | $R^5$ | $R^6$ | Assay Value |
|---|---|---|---|---|---|---|---|
| B-1 | $CH_3$ | $OCH_3$ | $OCH_3$ | $OCH_3$ | H | H | 96.8 |
| B-2 | H | $OCH_2CH_3$ | $OCH_3$ | H | H | H | >5 |
| B-3 | H | $OCH_3$ | OH | H | H | H | >5 |
| B-4 | H | H | $OCH_3$ | H | H | H | >5 |
| B-5 | $CH_3$ | $OCH_3$ | $OCH_2CH_3$ | H | H | H | >5 |
| B-6 | $CH_3$ | Cl | $OCH_3$ | H | H | H | >5 |
| B-7 | $CH_3$ | $OCH_3$ | O-acetyl | H | H | H | >5 |
| B-8 | H | Cl | Cl | H | H | H | >5 |
| B-9 | $CH_3$ | Br | $OCH_3$ | $OCH_3$ | H | H | >5 |
| B-10 | $CH_3$ | $OCH_2CH_3$ | H | H | H | H | 76.1 |
| B-11 | $CH_3$ | H | Br | H | H | H | 61.4 |
| B-12 | $CH_3$ | $OCH_3$ | $OCH_3$ | H | $OCH_3$ | H | 50.6 |
| B-13 | $(C=O)CH_2CH_3$ | $OCH_2CH_3$ | $OCH_3$ | Br | H | H | 62.2 |
| B-14 | $CH_3$ | H | $O(C=O)CH_3$ | $OCH_3$ | $NO_2$ | H | 61.1 |
| B-15 | $CH_3$ | H | H | $OCH_2CH_3$ | $O(C=O)CH_3$ | H | 53.1 |
| B-16 | H | H | O-cyclopentyl | H | H | H | 100 |
| B-17 | 2-Cl-benzyl | $OCH_3$ | $OCH_3$ | $OCH_3$ | H | H | 100 |
| B-18 | benzyl | $OCH_3$ | $O(C=O)CH_3$ | H | H | H | 100 |
| B-19 | H | H | O-benzyl | H | H | H | 91.0 |
| B-20 | $CH_3$ | $NO_2$ | H | H | H | H | 92.4 |
| B-21 | $CH_3$ | I | H | H | $O(C=O)CH_3$ | H | 72.5 |
| B-22 | $CH_3$ | Cl | H | $OCH_3$ | $O(C=O)CH_3$ | H | 98.1 |
| B-23 | $CH_3$ | Br | H | $OCH_3$ | $OCH_3$ | H | 72.8 |
| B-24 | $(C=O)CH_2CH_3$ | $OCH_3$ | $O(C=O)CH_2CH_3$ | $OCH_3$ | H | H | 98.1 |
| B-25 | 4-Cl-benzyl | $OCH_3$ | $O(C=O)CH_3$ | $OCH_3$ | H | H | 78.8 |
| B-26 | H | H | $CH_2CH_3$ | H | H | H | 81.1 |
| B-27 | H | Cl | H | Br | OH | H | 100 |
| B-28 | H | Cl | H | $OCH_3$ | $OCH_3$ | H | 100 |
| B-29 | $(C=O)CH_3$ | H | OH | $OCH_3$ | H | H | 94.2 |

TABLE 9-continued
B-I
| Compound No. | $R^1$ | $R^2$ | $R^3$ | $R^4$ | $R^5$ | $R^6$ | Assay Value |
|---|---|---|---|---|---|---|---|
| B-30 | H | H | O—CH$_2$—O | | H | H | 94.4 |
| B-31 | H | H | O-iso-propyl | H | H | H | 100 |
| B-32 | H | H | O-benzyl | OCH$_3$ | H | H | 91.8 |
| B-33 | H | CH$_3$ | OCH$_3$ | H | H | H | 90.7 |
| B-34 | H | OCH$_3$ | H | H | H | H | 51.8 |
| B-35 | H | OCH$_3$ | OCH$_3$ | OCH$_3$ | H | H | <5 |
| B-36 | H | OCH$_3$ | OH | OCH$_3$ | H | H | <5 |
The trans isomers of compounds B-1 through B-34 are also depicted below:
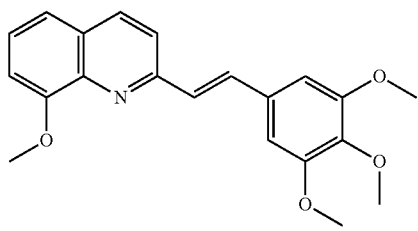
B-1
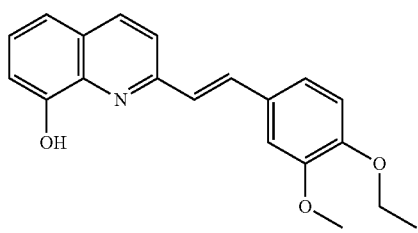
B-2
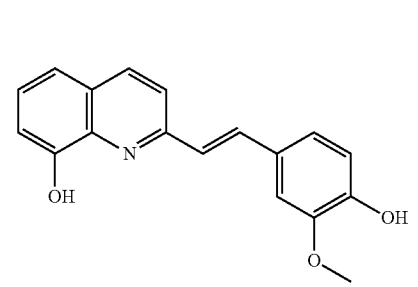
B-3
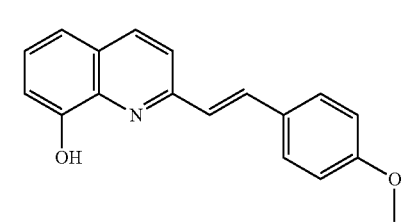
B-4
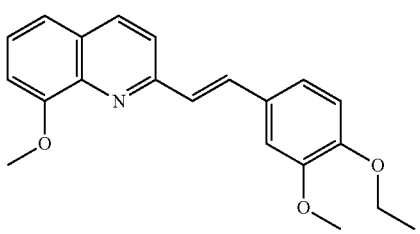
B-5
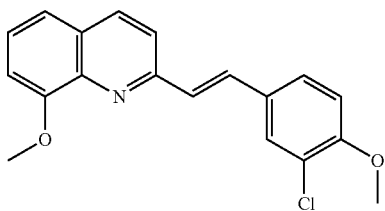
B-6
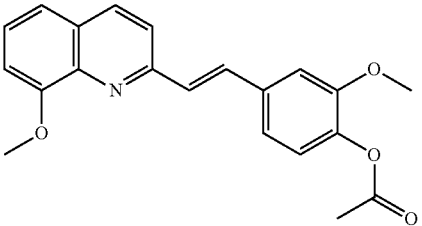
B-7
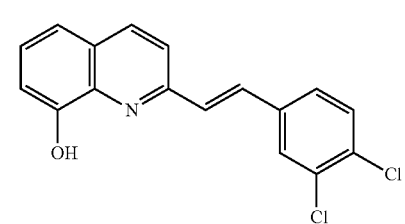
B-8

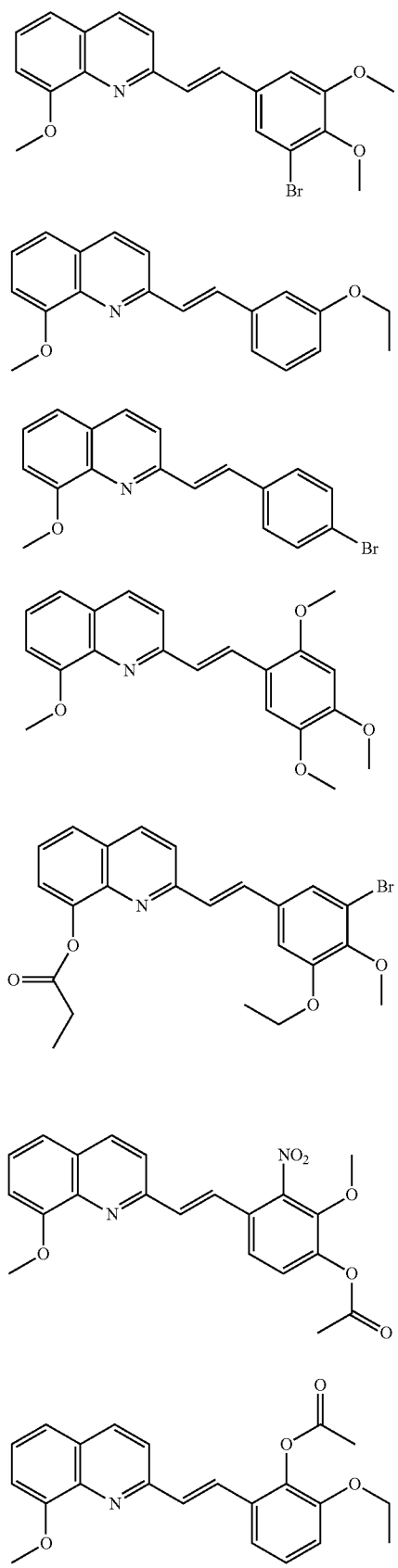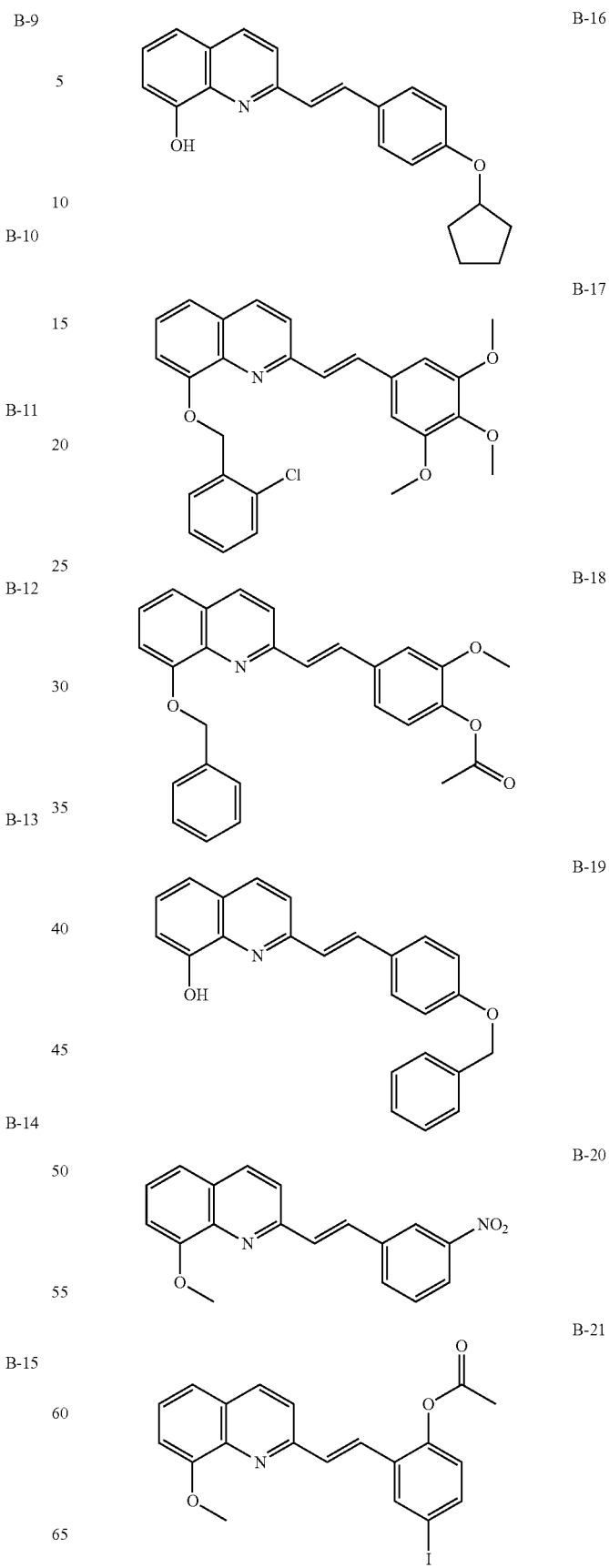

B-22 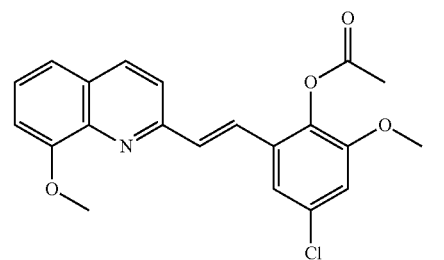
B-23 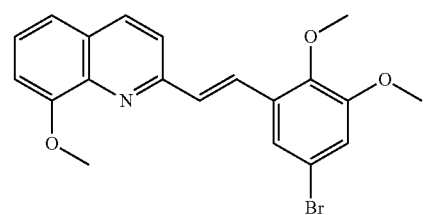
B-24 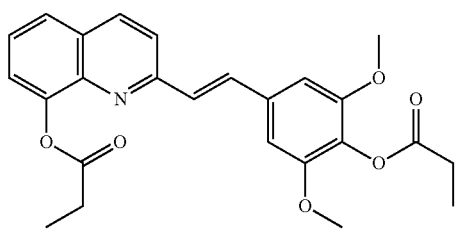
B-25 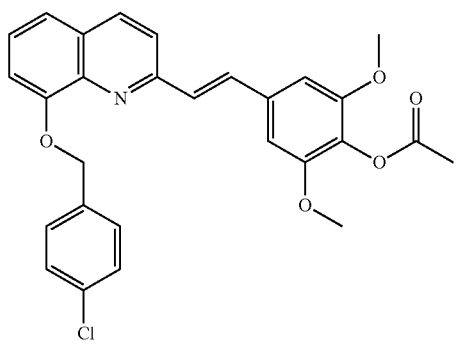
B-26 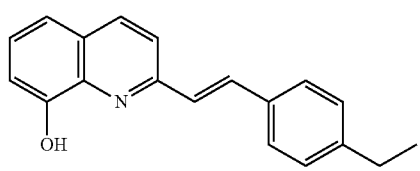
B-27 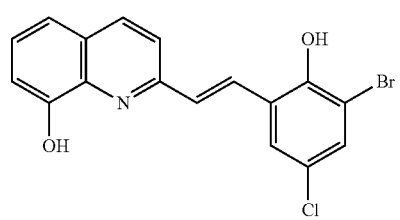
B-28 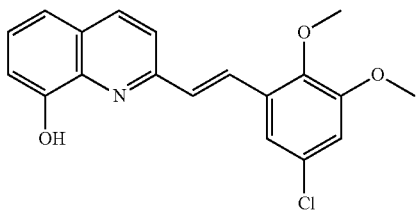
B-29 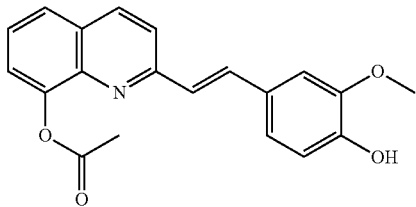
B-30 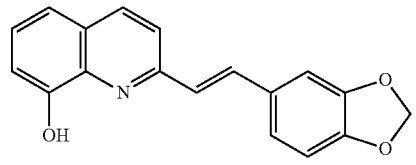
B-31 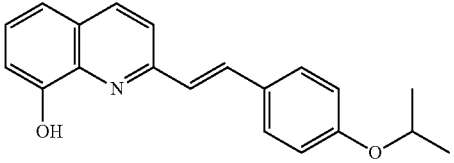
B-32 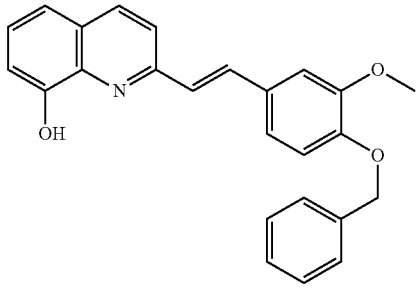
B-33 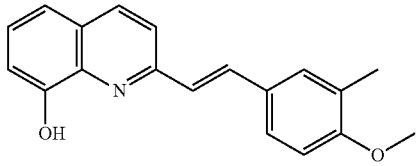
B-34 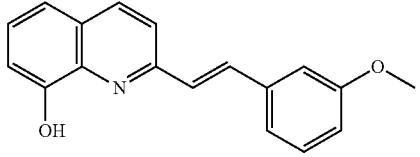
Illustrative examples of the compounds of Formula B-IIa are provided in Table 10.

TABLE 10

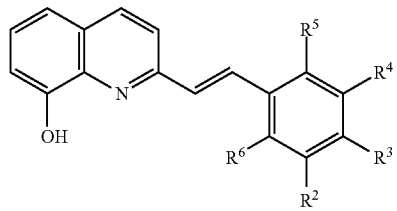

B-IIa

| Compound No. | $R^2$ | $R^3$ | $R^4$ | $R^5$ | $R^6$ | Assay Value |
|---|---|---|---|---|---|---|
| B-2 | OCH$_3$ | OCH$_2$CH$_3$ | H | H | H | >5 |
| B-3 | OCH$_3$ | OH | H | H | H | >5 |
| B-4 | H | OCH$_3$ | H | H | H | >5 |
| B-8 | Cl | Cl | H | H | H | >5 |
| B-16 | H | O-cyclopentyl | H | H | H | 100 |
| B-19 | H | O-benzyl | H | H | H | 91.0 |
| B-26 | H | CH$_2$CH$_3$ | H | H | H | 81.1 |
| B-27 | H | Cl | H | Br | OH | 100 |
| B-28 | Cl | H | OCH$_3$ | OCH$_3$ | H | 100 |
| B-30 | H | O—CH$_2$—O | H | H | H | 94.4 |
| B-31 | H | O-iso-propyl | H | H | H | 100 |
| B-32 | H | O-benzyl | OCH$_3$ | H | H | 91.8 |
| B-33 | CH$_3$ | OCH$_3$ | H | H | H | 90.7 |
| B-34 | OCH$_3$ | H | H | H | H | 51.8 |
| B-35 | OCH$_3$ | OCH$_3$ | OCH$_3$ | H | H | <5 |
| B-36 | OCH$_3$ | OH | OCH$_3$ | H | H | <5 |

Illustrative examples of the compounds of Formula B-IIb are provided in Table 11.

TABLE 11

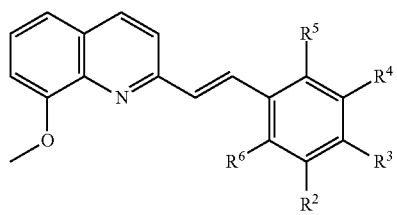

B-IIb

| Compound No. | $R^2$ | $R^3$ | $R^4$ | $R^5$ | $R^6$ | Assay Value |
|---|---|---|---|---|---|---|
| B-1 | OCH$_3$ | OCH$_3$ | OCH$_3$ | H | H | 96.8 |
| B-5 | OCH$_3$ | OCH$_2$CH$_3$ | H | H | H | >5 |
| B-6 | Cl | OCH$_3$ | H | H | H | >5 |
| B-7 | OCH$_3$ | O-acetyl | H | H | H | >5 |
| B-9 | Br | OCH$_3$ | OCH$_3$ | H | H | >5 |
| B-10 | OCH$_2$CH$_3$ | H | H | H | H | 76.1 |
| B-11 | H | Br | H | H | H | 61.4 |
| B-12 | OCH$_3$ | OCH$_3$ | H | OCH$_3$ | H | 50.6 |
| B-14 | H | O(C=O)CH$_3$ | OCH$_3$ | NO$_2$ | H | 61.1 |
| B-15 | H | H | OCH$_2$CH$_3$ | O(C=O)CH$_3$ | H | 53.1 |
| B-20 | NO$_2$ | H | H | H | H | 92.4 |
| B-21 | I | H | H | O(C=O)CH$_3$ | H | 72.5 |
| B-22 | Cl | H | OCH$_3$ | O(C=O)CH$_3$ | H | 98.1 |
| B-23 | Br | H | H | OCH$_3$ | OCH$_3$ | 72.8 |

Illustrative examples of the compounds of Formula B-IIc are provided in Table 12.

TABLE 12

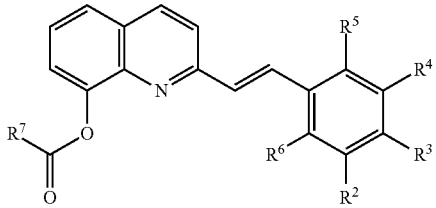

B-IIc

| Compound No. | $R^7$ | $R^2$ | $R^3$ | $R^4$ | $R^5$ | $R^6$ | Assay Value |
|---|---|---|---|---|---|---|---|
| B-13 | CH$_2$CH$_3$ | OCH$_2$CH$_3$ | OCH$_3$ | Br | H | H | 62.2 |
| B-24 | CH$_2$CH$_3$ | OCH$_3$ | O(C=O)CH$_2$CH$_3$ | OCH$_3$ | H | H | 98.1 |
| B-29 | CH$_3$ | H | OH | OCH$_3$ | H | H | 94.2 |

Illustrative examples of the compounds of Formula B-IId are provided in Table 13.

TABLE 13

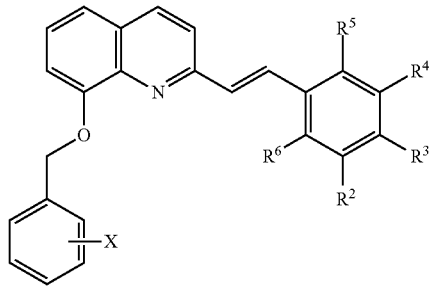

B-IId

| Compound No. | X | $R^2$ | $R^3$ | $R^4$ | $R^5$ | $R^6$ | Assay Value |
|---|---|---|---|---|---|---|---|
| B-17 | 2-chloro | OCH$_3$ | OCH$_3$ | OCH$_3$ | H | H | 100 |
| B-18 | | OCH$_3$ | O(C=O)CH$_3$ | H | H | H | 100 |
| B-25 | 4-chloro | OCH$_3$ | O(C=O)CH$_3$ | OCH$_3$ | H | H | 78.8 |

Compounds B-1 through B-36 are available from Chembridge Corporation, 16981 Via Tazon, Suite G, San Diego, Calif. 92127.

The compounds described above include the compounds themselves, as well as their salts and their prodrugs, if applicable. The salts, for example can be formed between a positively charged substituent (such as an amide) on a compound and an anion. Suitable anions include, but are not limited to, chloride, bromide, iodide, sulfate, nitrate, phosphate, citrate, methanesulfonate, tartrate, trifluoracetate, acetate, and the like.

Examples of prodrugs include esters, phosphonates, and other pharmaceutically acceptable derivatives, which, upon administration to a subject, are capable of providing the compounds described above.

In addition to the above-described compounds, salts, and prodrug forms, those forms may also be solvated and unsolvated (such as hydrates).

Formulations and Routes of Administration

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds of the invention include, but are not limited to Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon α-2a, α-2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, but are not limited to, tricyclic anti-depressant drugs (such as imipramine, desipramine, amitriptyline, clomipramine, trimipramine, doxepin, nortriptyline, protriptyline, amoxapine and maprotiline); non-tricyclic and anti-depressant drugs (such as sertraline, trazodone and citalopram); $Ca^{2+}$ antagonists (such as verapamil, nifedipine, nitrendipine and caroverine); Amphotericin (such as Tween 80 and perhexyline maleate); triparanol analogues (such as tamoxifen); antiarrhythmic drugs (such as quinidine); antihypertensive drugs (such as reserpine); thiol depleters (such as buthionine and sulfoximine); and calcium leucovorin.

The active compound(s) may be administered per se or in the form of a pharmaceutical composition wherein the active compound(s) is in admixture with one or more pharmaceutically acceptable carriers, excipients or diluents. Pharmaceutical compositions for use with the compounds described above may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee (tablet) cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant (such as dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection (such as by bolus injection or continuous infusion). Formulations for injection may be presented in unit dosage form (in ampoules or in multi-dose containers) with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension (such as sodium carboxymethyl cellulose, sorbitol, or dextran). Optionally, the suspension may also contain suitable stabilizers or agents which increase the solubility of the compounds to allow for the preparation of highly concentrated solutions.

Alternatively, the active ingredient may be in powder form for constitution with a suitable vehicle (such as sterile pyrogen-free water) before use.

The compounds may also be formulated in rectal compositions such as suppositories or retention enemas (such as containing conventional suppository bases like cocoa butter or other glycerides).

In addition to the formulations described previously, the compounds may also be formulated as a depot preparation. Such long acting formulations may be administered by implantation or transcutaneous delivery (such as subcutaneously or intramuscularly), intramuscular injection or a transdermal patch. Thus, the compounds may be formulated with suitable polymeric or hydrophobic materials (such as an emulsion in an acceptable oil) or ion exchange resins, or as sparingly soluble derivatives (such as a sparingly soluble salt).

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosages

Pharmaceutical compositions suitable for use with the compounds described above include compositions wherein the active ingredient is contained in a therapeutically effective amount (an amount effective to achieve its intended purpose). Of course, the actual amount effective for a particular application will depend on the condition being treated. For example, when administered in methods to inhibit cell proliferation, such compositions will contain an amount of active ingredient effective to achieve this result. When administered to patients suffering from disorders characterized by abnormal cell proliferation, such compositions will contain an amount of active ingredient effective to prevent the development of or alleviate the existing symptoms of, or prolong the survival of, the patient being treated. For use in the treatment of cancer, a therapeutically effective amount further includes that amount of compound which arrests or regresses the growth of a tumor. Determination of an effective amount is well within the capabilities of those skilled in the art.

For any compound described herein the therapeutically effective amount can be initially determined from cell culture arrays. Target plasma concentrations will be those concentrations of active compound(s) that are capable of inducing at least about 25% inhibition of MET receptor signaling and/or at least about 25% inhibition of cell proliferation in cell culture assays, depending, of course, on the particular desired application. Target plasma concentrations of active compound(s) that are capable of inducing at least about 50%, 75%, or even 90% or higher inhibition of MET receptor signaling and/or cell proliferation in cell culture assays are preferred. The percentage of inhibition of MET receptor signaling and/or cell proliferation in the patient can be monitored to assess the appropriateness of the plasma drug concentration achieved, and the dosage can be adjusted upwards or downwards to achieve the desired percentage of inhibition.

Therapeutically effective amounts for use in humans can also be determined from animal models. For example, a dose for humans can be formulated to achieve a circulating concentration that has been found to be effective in animals. Useful animal models for diseases characterized by abnormal cell proliferation are well-known in the art. In particular, the following references provide suitable animal models for cancer xenografts (Corbett et al., 1996, J. Exp. Ther. Oncol. 1:95-108; Dykes et al., 1992, Contrib. Oncol. Basel. Karger 42:1-22), restenosis (Carter et al., 1994, J. Am. Coll. Cardiol: 24(5):1398-1405), atherosclerosis (Zhu et al., 1994, Cardiology 85(6):370-377) and neovascularization (Epstein et al., 1987, Cornea 6(4):250-257). The dosage in humans can be adjusted by monitoring MET receptor signaling inhibition and/or inhibition of cell proliferation and adjusting the dosage upwards or downwards, as described above.

A therapeutically effective dose can also be determined from human data for compounds which are known to exhibit similar pharmacological activities. Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

When treating disorders characterized by abnormal cell proliferation, including cancer, a circulating concentration of administered compound of about 0.001 μM to 20 μM is considered to be effective, or about 0.1 μM to 5 μM.

Patient doses for oral administration of the compounds described herein for the treatment or prevention of cell proliferative disorders typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For other modes of administration, dosage amount and interval can be adjusted individually to provide plasma levels of the administered compound effective for the particular clinical indication being treated. For use in the treatment of tumorigenic cancers, the compounds can be administered before, during or after surgical removal of the tumor. For example, the compounds can be administered to the tumor via injection into the tumor mass prior to surgery in a single or several doses. The tumor, or as much as possible of the tumor, may then be removed surgically. Further dosages of the drug at the tumor site can be applied post removal. Alternatively, surgical removal of as much as possible of the tumor can precede administration of the compounds at the tumor site.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. Of course, many factors are important in determining a therapeutic regimen suitable for a particular indication or patient. Severe indications such as invasive or metastasized cancer may warrant administration of higher dosages as compared with less severe indications such early-detected, non-metastasized cancer.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$, with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, In: The Pharmacological Basis of Therapeutics, Ch. 1, p 1).

Screening

In another aspect, a method for identifying agents or compounds that inhibit cell proliferation of eukaryotic cells by c-met activation is disclosed. This method includes (a) providing an MDCK cell expressing a METprotein; (b) contacting the cell with a test compound; (c) contacting the cell with hepatocyte growth factor; (d) determining activation of the c-met pathway in the cell by measuring epithelial-mesenchymal transition of MDCK cells, wherein no appearance of detached migratory MDCK cells is indicative of a compound that inhibits epithelial-mesenchymal transition by c-met activation and wherein the appearance of detached migratory MDCK cells is indicative of a compound that does not inhibit c-met induced epithelial-mesenchymal transition.

The MDCK cell are epithelial cells derived from mammalian tissues.

In one embodiment, MDCK cells are seeded at confluency into the wells of a transwell filter in DMEM (Dulbecco's Modified Eagle's Medium) with culturing medium, 10% fetal bovine serum for example. Cells are cultured for a period to allow for formation of an epithelial tissue in culture, such as for 24 hours. Test compounds, dissolved in a suitable solvent such as DMSO, can be added to each test well to a desired concentration just before stimulation of c-met signaling. Hepatocyte growth factor (HGF) is then added to the culture. The MDCK cells are cultured for a desired time period, for example 24 hours.

Concurrently, controls treated with and without HGF and with no test compounds can also be prepared.

After post-HGF addition culturing, transwell filters are prepared by repeated washing using ice-cold solution, such as phosphate-buffered saline (PBS). The cells are then fixed with paraformaldehyde solution on ice for 15 minutes to the filters. After fixation, the transwell filters are again washed repeatedly with PBS followed by staining with, for example, crystal violet for a period of time, for example, 15 minutes. The transwell filters are again washed, this time with distilled water.

The upper surface of the transwell filters are then swabbed of cells using a cotton-tipped probe until clear, leaving only cells on the lower surface of the filter (those cells that have undergone EMT). Filters are then processed to examine MDCK cell migration.

Various techniques are available to examine MDCK cell migration. In some embodiments, the number of cells migrating can be quantified. This may be done using, for example, various spectroscopic techniques. The number of migrating cells may also be examined by the amount of staining, for example with crystal violet, on the underside of the filter. Densitometry measurements can be used to determine relative light transmission through the transwell filters, which is reduced with increased staining of cells on the underside of the filter. The relative light transmission (the densitometry data) can be normalized on a scale of 1 to 100, with the positive and negative controls setting the 1 and 100 values, respectively. For another example, the filter can be examined by light microscopy and the number of cells counted per area or number of fields examined. Another example is to re-dissolve the stain on each filter in equal volumes of 10% acetic acid and measure the stain concentration in samples derived from each filter.

In some embodiments, the number of cells migrating can be determined using visual assessment. These techniques include visual inspection and assessments, such as using a microscope to identify cells appearing on the underside of the filter.

The appearance of a significant number of detached, migratory MDCK cells using qualitative or quantitative approaches is indicative of a compound that does not treat cancer (does not inhibit c-met induced epithelial-mesenchymal transition). The absence of a quantitatively identifiable or significant number of detached, migratory MDCK cells is indicative of a compound that treats cancer (inhibits epithelial-mesenchymal transition by c-met activation). The use of controls, including negative controls where cells are not treated with HGF, provide one of ordinary skill with qualitative and quantitative references points to determine qualitatively identifiable and statistically significant experimental variation. In addition, acceptable standards of recognizing statistically significance and qualitative identification are known to one of ordinary skill.

EXAMPLES

MDCK cells were seeded at confluency into the wells of a transwell filter in DMEM with 10% fetal bovine serum. Cells were cultured for 24 hours. Test compounds, dissolved in DMSO, were added to each test well to a 10 µM final concentration, and then hepatocyte growth factor (HGF) was then added. The MDCK cells were cultured for 24 hours. Concurrently, controls treated with and without HGF and with no test compounds were also prepared.

After post-HGF addition culturing, transwell filters were prepared by repeated washing using ice cold PBS. The cells were then fixed with paraformaldehyde (3.7%) on ice for 15 minutes to the filters. After fixation, the transwell filters were washed repeatedly with PBS followed by staining with crystal violet for 15 minutes. The transwell filters were washed again with distilled water.

The upper surface of the transwell filters were swabbed using a cotton-tipped probe. The filters were photographed using a gel documentation system. Densitometry measurements were made on the test samples and compared with control samples. Controls, namely unstimulated cells and hepatocyte growth factor (HGF) treated cells that had not received any compound treatment, were used to calibrate a maximal and nil effect, respectively.

Assay values, reported as a percentage value like the untreated controls, for tested compounds are reported in Tables 1-11 above. Compounds listed in the tables as having an assay value greater than 5 indicate compounds that prevent detachment of migratory MDCK cells in response to activation of the c-met pathway (they thus inhibit epithelial-mesenchymal transition). Compounds listed with assay values less than 5 indicate a compound that does not prevent cells from undergoing EMT in response to activation of the c-met pathway (with appearance of detached migratory MDCK cells).

The invention claimed is:

1. A method for inhibiting cellular responses to MET receptor signaling by administering a compound selected from the group consisting of:

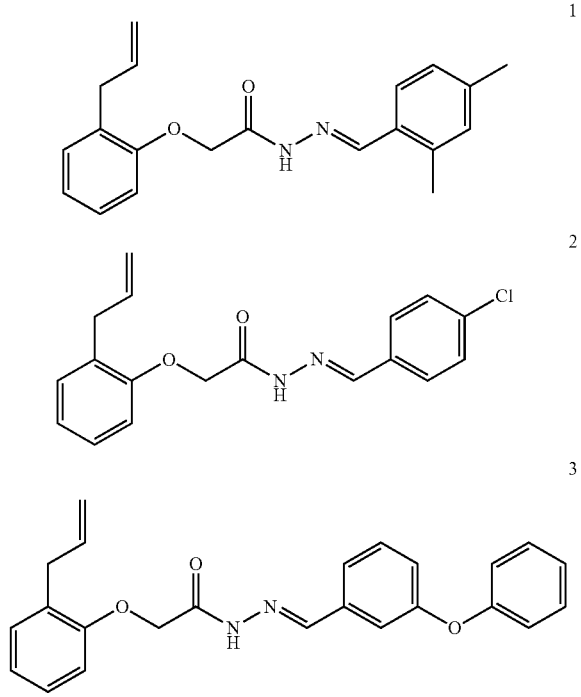

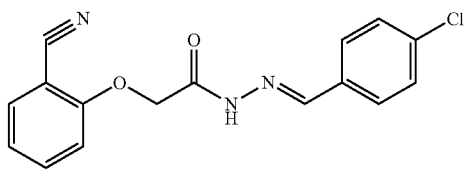

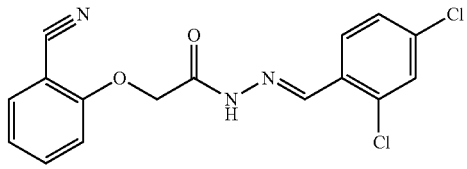

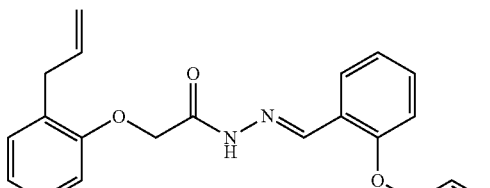

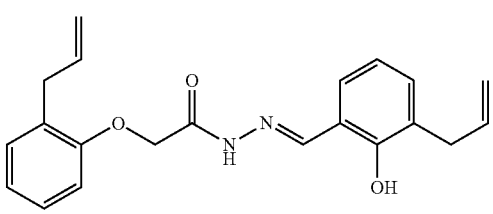

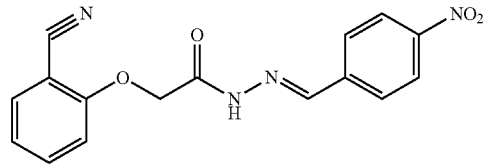

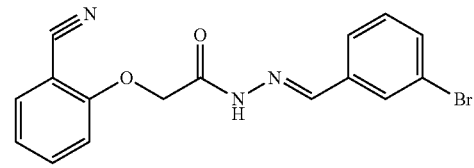

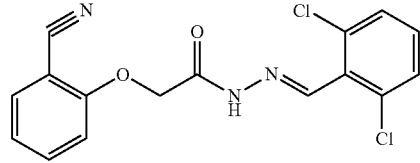

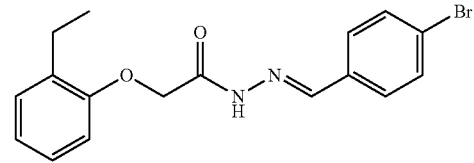

-continued

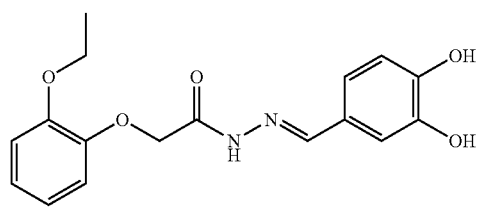

and pharmaceutically acceptable salts thereof.

2. The method of claim 1, wherein the compound is

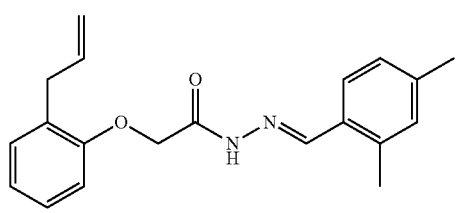

and pharmaceutically acceptable salts thereof.

3. The method of claim 1, wherein the compound is

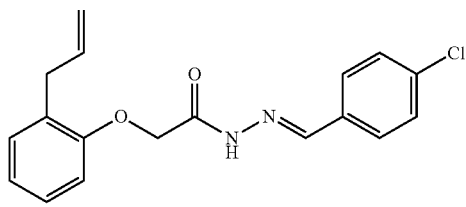

and pharmaceutically acceptable salts thereof

4. The method of claim 1, wherein the compound is

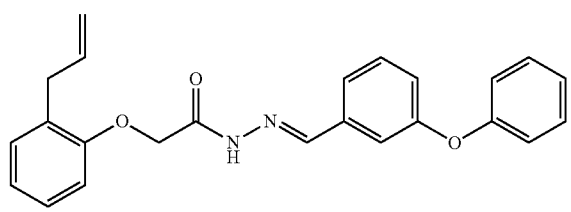

and pharmaceutically acceptable salts thereof.

5. The method of claim 1, wherein the compound is

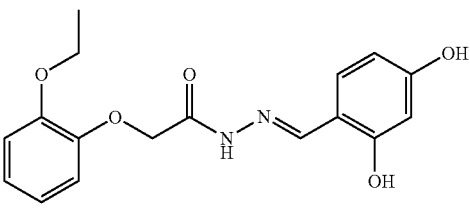

and pharmaceutically acceptable salts thereof.

6. The method of claim 1, wherein the compound is

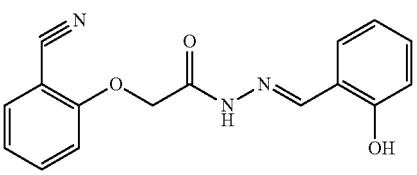

and pharmaceutically acceptable salts thereof.

7. The method of claim 1, wherein the compound is

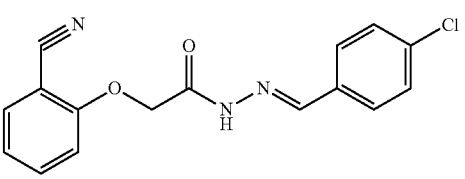

and pharmaceutically acceptable salts thereof.

8. The method of claim 1, wherein the compound is

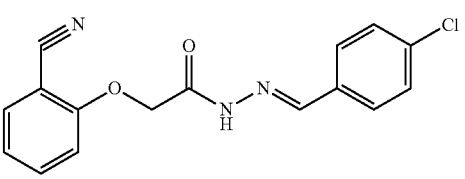

and pharmaceutically acceptable salts thereof.

9. The method of claim 1, wherein the compound is

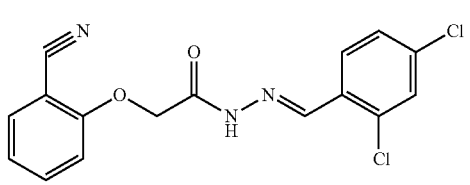

and pharmaceutically acceptable salts thereof.

10. The method of claim 1, wherein the compound is

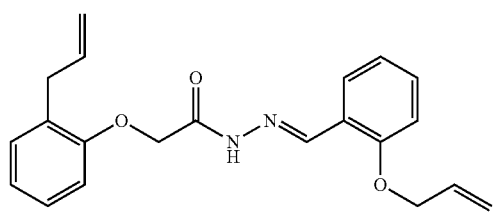

and pharmaceutically acceptable salts thereof.

11. The method of claim 1, wherein the compound is

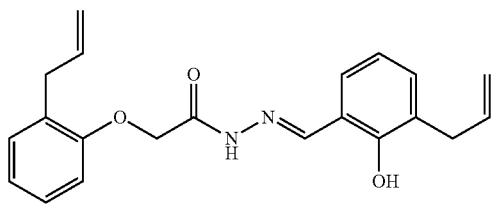

and pharmaceutically acceptable salts thereof.

12. The method of claim 1, wherein the compound is

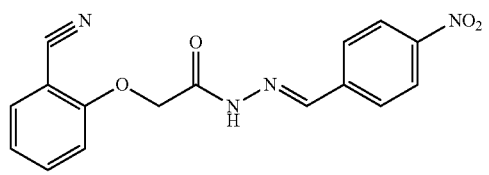

and pharmaceutically acceptable salts thereof.

13. The method of claim 1, wherein the compound is

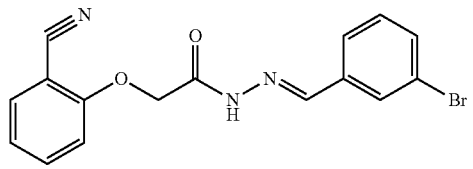

and pharmaceutically acceptable salts thereof.

14. The method of claim 1, wherein the compound is

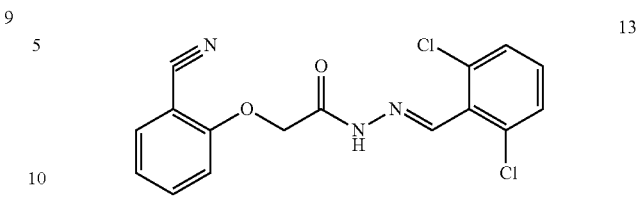

and pharmaceutically acceptable salts thereof.

15. The method of claim 1, wherein the compound is

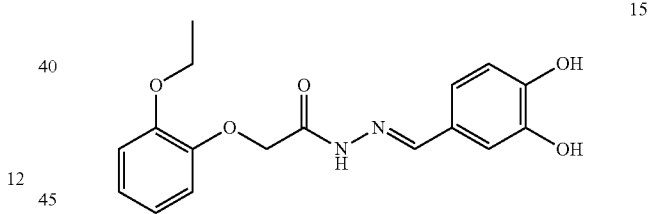

and pharmaceutically acceptable salts thereof.

16. The method of claim 1, wherein the compound is

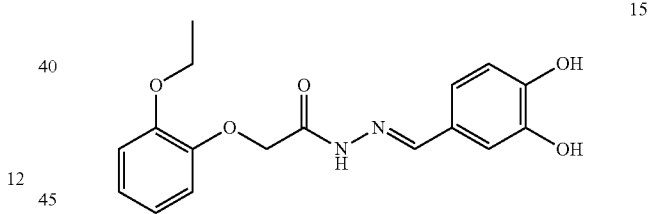

and pharmaceutically acceptable salts thereof.

* * * * *